USOO5543111A

United States Patent [19]
Bridges et al.

[11] Patent Number: 5,543,111
[45] Date of Patent: Aug. 6, 1996

[54] METHOD AND APPARATUS FOR RENDERING MEDICAL MATERIALS SAFE

[75] Inventors: Jack E. Bridges, Park Ridge; Guggilam C. Sresty, Burbank; Jeffrey S. Held, Chicago; James W. Sharp, Arlington Heights; Thomas J. Bajzek, Woodale, all of Ill.

[73] Assignee: IIT Research Institute, Chicago, Ill.

[21] Appl. No.: 290,002

[22] Filed: Aug. 12, 1994

Related U.S. Application Data

[63] Continuation of Ser. No. 193,724, Feb. 9, 1994, abandoned, which is a continuation of Ser. No. 77,046, Jun. 15, 1993, abandoned, which is a continuation of Ser. No. 549,576, Jul. 6, 1990, abandoned.

[51] Int. Cl.$^6$ ........................................... A61L 2/08
[52] U.S. Cl. ........................ 422/22; 204/164; 250/455.1; 250/492.1
[58] Field of Search ..................... 422/20–23; 204/164; 250/455.11, 492.1

[56] References Cited

U.S. PATENT DOCUMENTS

| | | |
|---|---|---|
| 2,114,345 | 4/1938 | Hayford . |
| 2,486,684 | 11/1949 | Schlesman et al. . |
| 2,731,208 | 1/1956 | Dodd . |
| 3,095,359 | 6/1963 | Heller . |
| 3,215,539 | 11/1962 | Landy . |
| 3,261,140 | 7/1966 | Long et al. . |
| 3,490,580 | 1/1970 | Brumfield et al. . |
| 3,494,723 | 2/1970 | Gray . |
| 3,494,724 | 2/1970 | Gray . |
| 3,547,577 | 12/1970 | Lovercheck . |
| 3,551,090 | 12/1970 | Brumfield et al. . |
| 3,602,712 | 8/1971 | Mann et al. . |
| 3,617,178 | 11/1971 | Clouston . |
| 3,704,089 | 11/1972 | Stehlik . |
| 3,753,651 | 8/1973 | Boucher . |
| 3,885,915 | 5/1975 | Utsumi et al. . |
| 3,926,556 | 12/1975 | Boucher . |
| 3,940,325 | 2/1976 | Hirao . |
| 3,948,601 | 4/1976 | Fraser et al. . |
| 3,958,936 | 5/1976 | Knight . |
| 4,151,419 | 4/1979 | Morris et al. . |
| 4,207,286 | 6/1980 | Boucher . |
| 4,250,139 | 2/1981 | Luck et al. . |
| 4,400,357 | 8/1983 | Hohmann . |
| 4,457,221 | 7/1984 | Geren . |
| 4,524,079 | 6/1985 | Hofmann . |
| 4,530,908 | 7/1985 | Strand .................................. 436/536 |

(List continued on next page.)

FOREIGN PATENT DOCUMENTS

| | | |
|---|---|---|
| 1123705 | 11/1984 | U.S.S.R. . |
| 942374 | 11/1963 | United Kingdom . |
| 1406789 | 9/1975 | United Kingdom . |
| PCT/US91/02196 | 3/1991 | WIPO . |
| PCT/US91/04703 | 10/1991 | WIPO . |

OTHER PUBLICATIONS

"Progress Report: Beneficial Uses Program, Period ending Dec. 31, 1976", Waste Management and Environmental Programs Department, Sandia Laboratories, SAND77–0426 (1977).

Chipley, J., "Effects of Microwave Irradiation on Microorganisms", Advances in Applied Microbiology, vol. 26, pp. 129–145 (1980).

(List continued on next page.)

*Primary Examiner*—Lyle A. Alexander
*Attorney, Agent, or Firm*—Fitch, Even, Tabin & Flannery

[57] ABSTRACT

Infectious medical materials are rendered harmless by heating heterogeneous medical materials having wet and dry portions with a radio-frequency electric field. The medical materials may be comminuted prior to heating. The medical materials are exposed to the radio-frequency electric field in order to heat the medical materials. The medical materials may include sorted medical or veterinary waste which after heat treatment may be recycled.

10 Claims, 15 Drawing Sheets

U.S. PATENT DOCUMENTS

| | | |
|---|---|---|
| 4,552,720 | 11/1985 | Baker et al. . |
| 4,563,259 | 1/1986 | Rayner ................................. 524/99 |
| 4,569,736 | 2/1986 | Kosegaki et al. ................. 523/105 |
| 4,599,216 | 7/1986 | Rohrer et al. . |
| 4,620,908 | 11/1986 | Van Duzer . |
| 4,652,763 | 3/1987 | Nablo . |
| 4,671,935 | 6/1987 | Rohrer et al. . |
| 4,746,968 | 5/1988 | Wear et al. . |
| 4,775,770 | 10/1988 | Fritz . |
| 4,801,427 | 1/1989 | Jacob . |
| 4,808,782 | 2/1989 | Nakagawa et al. . |
| 4,808,783 | 2/1989 | Stenström . |
| 4,818,488 | 4/1989 | Jacob . |
| 4,896,010 | 1/1990 | O'Connor et al. . |
| 4,917,586 | 4/1990 | Jacob . |
| 4,931,261 | 6/1990 | Jacob . |
| 4,943,417 | 7/1990 | Jacob . |
| 4,978,501 | 12/1990 | Diprose et al. . |
| 4,984,748 | 1/1991 | Kimura ................................. 241/65 |
| 5,019,344 | 5/1991 | Kutner et al. . |
| 5,035,858 | 7/1991 | Held et al. ........................... 422/21 |
| 5,106,594 | 4/1992 | Held et al. ......................... 422/292 |
| 5,226,065 | 7/1993 | Held et al. ........................... 378/64 |

OTHER PUBLICATIONS

Sivinksi, J., "General Description of the Sludge Irradiation Process", National Symposium on the Use of Cesium–137 to Process Sludge for Further Reduction of Pathogens, SAND80–2744 (Dec. 1980).

Tonetti, R., "Disease Control Requirements for Various Sludge Uses", National Symposium on the Use of Cesium–137 to Process Sludge for Further Reduction of Pathogens, SAND80–2744 (Dec. 1980).

"Dielectric Heating: RF and Microwave", EPRI Center for Materials Fabrication, Tech Commentary, vol. 4, No. 1 (1987).

"Gamma Processing Equipment", AECL Industrial Radiochemical Co., Irradiation Division product brochure (Jan. 1987).

Paul, B., "Combustion Says Firm Sterilizes Medical Waste with Microwaves", Wall Street Journal, Apr. 10, 1989, p. B3.

"A Microwave Sterilizer is Developed", New Youk Times, Science Watch, Jun. 20, 1989.

Hall, Steven K., "Infectious Waste Management: A Multifaceted Problem," Pollution Engineering, 74–78 (Aug. 1989).

"Medical Waste Treatment by Microwave Technology", product brochure, Norcal Solid Waste Systems, publication date unknown.

"Dielectric Heating", product brochure, PSC, Inc., publication date unknown.

Ward, J., "Molecular Mechanisms of Radiation–Induced Damage to Nucleic Acids", unknown source and publication date.

"Electromagnetic Radiation and Ionizing Energy", unknown source and publication date.

Serota, "Heating with Radio Waves," *Automation* (Sep. 1973).

Reynolds et al., "Thermoradiation Inactivation of Naturally Occurring Bacterial Spores in Soil," *Applied Microbiology*, vol. 28, No. 3 (Sep. 1974), pp. 406–410.

Brannen, "A Kinetic Model for the Biological Effects of Ionizing Radiation," *Report No. SAND74–0269*, Sandia Laboratories, Albuquerque, New Mexico, printed Oct. 1974, pp. 1–38.

Markitanova et al., "Study of Reagentless Sterilization of Wastewaters," *Journal of Applied Chemistry of the U.S.S.R.*, vol. 59, No. 11/Part 2 (Nov. 1986), pp. 2365–2368.

United States Pharmacopeia XX: Section 1211, "Sterilization," pp. 1037–1040.

Morganstern, "Future of Radiation Sterilization," Second Johnson and Johnson Conference on Sterilization of Medical Products by Ionizing Radiation (held in Vienna, Austria, Apr. 25–28, 1977), pp. 1–26, publication date Jun. 15, 1977.

"Mechanism of Microwave Sterilization in the Dry State", unknown source and publication date.

Christensen et al., "The Multi–Purpose Irradiation Plant and the Quality Control of Radiation Sterilization of Medical Equipment, " *Proceedings of the Fourth International Conference on the Peaceful Uses of Atomic Energy* (held in 1971), vol. 14 (1972), pp. 345–354.

Centers for Materials Fabrication, "Dielectric Heating: RF and Microwave", vol. 4, No. 1, pp. 2–4, 1987.

"Sterling's Elutriator, " Sterling Systems, A Division of The Sterling Blower Company, Forest, Va. No Publication Date Supplied.

"Innovative Technology From The Sterling Blower Company," Sterling Systems, A Division of The Sterling Blower Company, Forest, Va. No Publication Date Supplied.

International Search Report for international application No. PCT/US91/04755, which corresponds to the instant application, mailed on 10 Oct. 1991.

Written Opinion issued pursuant to PCT Rule 66.2 or 66.4(a) for international application No. PCT/US91/04755, which corresponds to the instant application, mailed on 8 May 1992.

(a) TE$_{10}$ MODE POWER DENSITY (b) TE$_{20}$ MODE POWER DENSITY (c) 0.864 TE$_{10}$ + 0.48 TE$_{20}$ POWER DENSITY

METHOD AND APPARATUS FOR RENDERING MEDICAL MATERIALS SAFE

This application is a continuation of application Ser. No. 193,724 filed Feb. 9, 1994 now abandoned, which is a continuation of application Ser. No. 77,046 filed Jun. 15, 1993 now abandoned, which is a continuation of application Ser. No. 07/549,576 filed Jul. 6, 1990, now abandoned.

BACKGROUND OF THE INVENTION

The present invention relates generally to a method of disinfecting medical materials and more particularly to a method and apparatus for disinfecting medical materials by exposing the materials to radio-frequency waves. The term medical materials encompasses medical waste, veterinary waste, and medical products.

The problems with current medical waste handling methods, like the problems of solid waste disposal in general, are becoming increasingly acute. Solid waste is primarily disposed of by burning or by burial in landfill. Both of the methods have severe disadvantages. Burning of solid waste liberates waste particles and fumes which contribute to acid rain and other pollution of the atmosphere. Burying the waste results in possible leaks of toxic chemicals into the surrounding earth and contamination of ground water supplies. Although increasing amounts of solid waste are being recycled, which alleviates the problems of incineration and burial, presently available recycling methods do not provide a complete solution to the disposal problem.

Waste disposal is of even more urgent concern when the waste comprises possibly infectious medical waste. Such infectious medical waste is a by-product of veterinary and medical care. For example, regulated medical waste consists of: (1) cultures and stocks of infectious agents and associated biological materials; (2) pathological wastes; (3) human blood and blood products; (4) contaminated sharps, including needles, syringes, blades, scalpels, and broken glass; (5) animal waste; (6) isolation waste, including gloves and other disposable products used in the care of patients with serious infections; and (7) unused sharps. These wastes can generally be divided between (a) general medical waste, including cultures and stocks of infectious agents, associated biologicals, pathological waste, and human blood and blood products; (b) veterinary waste, including animal waste; and (c) waste that is predominately plastic, such as the contaminated and unused sharps and isolation waste. The predominately plastic waste also includes metal as well. Hospitals typically segregate waste by types. Contaminated sharps and isolation waste, however, are of special concern as they may carry highly dangerous pathogens such as AIDS virus or hepatitis virus. Sharps in particular have caused widespread public concern when observed washed up on beaches or in public areas.

Hospitals and other generators of medical and veterinary waste employ three methods of waste handling: (a) on-site incineration of the waste, (b) on-site steam autoclaving of the waste followed by later shipment to a landfill for burying, and (c) collection of the waste by a licensed waste hauler with no on-site processing.

Many hospital incinerators, even those located predominately in urban areas, emit pollutants at a relatively high rate. The Environmental Protection Agency has identified harmful substances in the emissions of such hospital incinerators. They include metals such as arsenic, cadmium and lead, organic compounds, such as ethylene, dioxins and furans, acid gases and carbon monoxide as well as soot, viruses and pathogens. Emissions from these incinerators may be a more significant public health hazard than improper dumping [Steven K Hall, "Infectious Waste Management: A Multifaceted Problem, " Pollution Engineering, 74–78 (August 1989)].

Although steam autoclaving may be used to sterilize waste before further processing, it is expensive and time consuming. Heat denatures the proteins and microorganisms causing protein inactivation and cell death in a short time. Temperature monitoring devices such as thermocouples, and biological indicators, such as heat resistant *Bacillus stearothermophilus* spores, may be used to assure effective sterilization.

U.S. Pat. No. 2,731,208 to Dodd teaches a steam sterilizing apparatus for disposing of contaminated waste which incorporates shredding the waste ("including paper containers such as used sputum cups," col. 1, lines 28–29). Dodd teaches blowing steam into a container full of waste and processing only limited types of items. The Dodd system has the disadvantage of depositing the shredded final mixture into a sewer, which would cause further environmental problems.

Whether or not the hospital first autoclaves its medical wastes, including broken needles and glass, the waste is then turned over to a licensed waste hauler for transport to a landfill or other depository. U.S. Pat. No. 3,958,936 to Knight discloses compaction of hospital waste for more efficient landfill disposal. Specifically, the reference teaches the application of heat in the range of about 204° C. to 316° C. to hospital and other waste to melt the plastic and convert it into a hard compact block for safer disposal in landfills. The waste is disinfected by the high temperatures, and sharps, such as needles, become embedded in the plastic where they are a reduced mechanical hazard. However, this method suffers from the disadvantage of requiring relatively high temperatures necessitating large energy expenditures and landfill disposal. Metropolitan landfills are becoming filled, and unauthorized dumping is a problem.

A further area of concern is the sterilization of medical products prior to use. By medical product is meant any product which must be sterilized prior to use in health care. This is exemplified but not limited to needles, syringes, sutures, bandages, scalpels, gloves, drapes, and other disposal items. Many reusable items also must be provided in sterile form. Widespread current sterilization methods include the use of autoclaving, ethylene oxide, and ionizing radiation such as gamma radiation. The heat and humidity of autoclaving are quite damaging to many disposable metal products. Ethylene oxide and ionizing radiation are preferred commercially in those cases.

In order to sterilize medical products, poisonous ethylene oxide gas may be used in a closed chamber containing the products to be sterilized. For effective sterilization, not only must the ethylene oxide concentration be controlled carefully, but the temperature, humidity, and porosity of the sterilizer load also must be carefully regulated. Ethylene oxide is relatively slow to dissipate from plastics and its use may require that medical products be stored until the ethylene oxide concentration decreases to a safe level. Ethylene oxide also must be carefully vented to the atmosphere subsequent to the sterilization cycle in order to avoid poisoning operators of the sterilization apparatus.

Ionizing radiation, such as gamma radiation, may be used to sterilize medical products within their packaging; however, it must be administered at such high doses that many plastics become yellow and brittle due to the gamma rays having altered the structure of the polymers of which they are made. For example, U.S. Pat. No. 3,940,325 to Hirao teaches methods for adjusting the formulas of plastics for medical syringes to avoid yellowing and cracking due to exposure to sterilizing gamma radiation. Other substances may also be damaged by exposure to gamma radiation. Such ionizing radiation sterilizes because its high energy photons damage and thereby inactivate the DNA of organisms such as bacteria and viruses. As a result of the inactivation of the DNA, cells lose their ability to reproduce and thereby cause infections. On a large scale industrial basis, ionizing radiation, especially gamma radiation from cobalt 60, has been used to sterilize medical products prior to their use in patients. However, the radiation levels necessary to sterilize may also damage the product being sterilized.

Other methods have been suggested for sterilization of medical products. For instance, U.S. Pat. No. 3,617,178 to Clouston teaches a method of improving sterilization efficiency by increasing hydrostatic pressure. Elevated hydrostatic pressure causes sterilization resistant bacterial spores to germinate, or begin to grow. However, it has no effect on viruses. Bacterial germination, which converts the bacteria from their environmentally resistant spore form, makes the bacteria more sensitive to radiation, so that lower doses may be employed. Clouston further teaches optimizing the hydrostatic pressure effect by adjusting the temperature up to 80° C. According to Clouston, elevated pressure in heated fluid or moist gas is essential to the method. Elevated temperature alone has a negligible effect. Furthermore, the pressure, heat, or moisture treatment taught by Clouston is intended to cause bacterial spores to germinate thereby rendering them more vulnerable to sterilization techniques, not to sterilize or inactivate microorganisms.

In contrast, Van Duzer U.S. Pat. Nos. 4,620,908 and Stehlik U.S. Pat. No. 3,704,089 teach prefreezing injectable proteins and surgical adhesive prior to irradiation with gamma radiation from cobalt 60 for aseptic manufacture of those materials. U.S. Pat. No. 3,602,712 to Mann discloses an apparatus for gamma irradiation and sterilization of sewage and industrial waste.

Besides gamma radiation, other types of electromagnetic radiation have been considered as potential sterilants in known systems. Microwaves are increasingly being investigated for rapid sterilization of individual medical devices as well as shredded medical waste. Recently, an experiment showed that metallic instruments could be sterilized in only 30 seconds in a microwave oven (New York Times, "Science Watch Microwave Sterilizer is Developed," Jun. 20 1989). That particular method, however, suffers from the drawback that only a few such metallic instruments can be treated at a particular time. It is not particularly applicable for treatment of medical waste in bulk, and in particular for treatment of medical waste which has been bagged.

United Kingdom Patent No. 1 406 789 to Boucher discloses a microwave system for the surface sterilization of reusable laboratory, medical, and dental instruments in a moist atmosphere at a lower temperature than those presently used and in a shorter time. The system is intended to render aseptic reusable instruments for medical use and generates electromagnetic energy having frequencies between 100 megahertz and 23000 megahertz. Boucher emphasizes that "his invention deals exclusively with surface sterilization" and that he "does not intend to cover such special cases" as "'in-depth' sterilization" (page 1, lines 58–67). Boucher teaches that only through a combination of proper humidification with the thermal and nonthermal effects of microwave radiation can reproducible and satisfactory results be obtained with a wide variety of species, including thermoresistant spores" (page 1, lines 77–83). Boucher teaches the placement of the object to be sterilized in a gas-tight container with a source of water vapor.

Soviet Union Patent No. 1,123,705 also discloses a method of sterilizing medical instruments for reuse by UHF treatment. For injection needles it discloses a final temperature of 160° C. to 470° C. and for acupuncture needles it discloses a final temperature of 160° C. to 270° C.

Systems are also known for treatment of disposable medical waste utilizing microwaves. This system first shreds the waste, sprays the shredded waste with water, and passes the wet shredded waste through a microwave chamber designed to raise the temperature of the wet shredded waste to 205° C. to sterilize it. After the sterilization step, the system compresses the sterilized shredded waste and packages it for shipment to landfills or incinerators (*The Wall Street Journal*, p. B-3, Apr. 10, 1989). One potential problem with this system is that shredding before sterilization could release infectious particles to the environment and may thus spread contagion. Another problem is the ultimate disposal of the waste; it persists in landfills or may pollute the air when incinerated.

Also of interest is a method and apparatus for using microwave frequency electromagnetic fields to heat medical waste to disinfect it. "Medical Waste Treatment By Microwave Technology", Norcal Solid Waste Systems. The system includes equipment for receiving the medical waste, shredding it into particle sizes of 1 to 1½ inch linear dimension, and applying steam to the shredded waste to increase its moisture content, as well as to inactivate certain of the microorganisms thereon. The waste is then carried to a microwave treatment area where microwave energy heats the waste to 203° C. for a selected amount of time. A holding area may provide heat sealing. The waste is then recirculated to the steaming station where steam is again applied to inactivate further microorganisms which may still be active in the waste which is shredded and disinfected, disposed in a dumpster for placement in a landfill. It may be appreciated, however, that volumetric heating cannot take place in such a microwave system that the waste has to be scattered in a relatively thin layer on a conveyor belt for treatment by the microwave radiation as the microwave radiation does not adequately penetrate the material. In addition, the material is not enclosed so that there is no substantial transfer of moisture from wet materials to dry materials to aid in the heating within the enclosed system.

U.S. Pat. No. 3,547,577 to Lovercheck discloses a machine for treating garbage by shredding, compressing the shredded garbage into briquettes, and sterilizing the briquettes with gas. After shredding the garbage is separated into magnetic and nonmagnetic portions. The sterilization step employs ethylene oxide gas which requires temperature control. The briquettes are maintained at a temperature of about 54° C.

Further, microwaves are limited in their penetration and are ineffective for heating when applied to large scale, boxed medical waste of the type which comprises the waste disposal problem today. Microwaves do not heat very effectively because they do not penetrate very deeply. Most of the heat is generated near the surface and quickly dissipates into the surroundings, in part because it is not well conducted into the center portions of the boxed medical waste. In contrast, radio-frequency waves at relatively low frequency can penetrate boxed medical waste more deeply.

It also is known in the art that thermal radiation treatment of bacterial spores and other pathogens may allow greatly reduced ionizing radiation dosage to accomplish sterilization of a given population. For instance, in "Thermoradiation Inactivation Of Naturally Occurring Bacterial Spores In Soil, . . . " M. C. Reynolds et al , *Applied Microbiology,* Vol 28, No. 3, September 1974, it is disclosed that bacterial spores may be inactivated by heating them with dry heat and exposing them to ionizing radiation from a cobalt 60 source allow greatly reduced treatment times over the use of either dry heat or radiation alone.

An attempt to elucidate a model for such behavior is set forth in J. P. Brannen, "A Kinetic Model For The Biological Effects Of Ionizing Radiation", Sandia Laboratories, SAND74-0289 (October 1974).

Heat and radiation inactivation of bacteria are discussed at "Progress Report Beneficial Uses Program, Period Ending Dec. 31, 1976", Waste Management and Environmental Programs Department, Sandia Laboratories, SAND77-0426 (1977), where it is taught that viruses in sewage sludge may be destroyed by evaporation. Heat inactivation may be used to destroy Salmonella enterititis ser. montevideo. Streptococcus bacteria may be destroyed by using ionizing radiation at a dose of about 140 kilorads.

The use of cesium 137 to inactivate pathogens in sludge is discussed in "Sludge Or Radiation Disinfection For Beneficial Use", Applied Biology And Isotope Utilization Division 4535, "General Description of the Sludge and Radiation Process" SAND80-2744 (December 1980), where it is disclosed that cesium-137, emitting gamma radiation may be used to inactivate pathogens in sewage sludge. See also, "Use Of Cesium-137 to Process Sludge for Further Reduction of Pathogens, Sludge or Radiation Disinfection for Beneficial Use," Disease Control Requirements for Various Sludge Uses, Applied Biology and Isotope Utilization Division 4535, SAND80-2744 (Dec. 1980), which discloses that in order to render sewage sludge safe, in particular for certain agricultural usages, irradiation may be used as an add-on process in conjunction with sterilization where sludge is maintained at 30 min. at a temperature of at least 70° C. In each of the aforementioned papers, it may be appreciated that the sludge which is being treated is substantially homogeneous in its dielectric characteristics and, thus, in its heating characteristics.

The gamma irradiation equipment commonly used and disclosed in this application is of the type disclosed in "Gamma Processing Equipment", AECL Industrial and Radiation Division (January 1987).

The dual plate about 12 megahertz plate type radio-frequency heater is of the type disclosed in "Dielectric Heating" PSC Inc which although undated, constitutes prior art to this application.

Like microwaves, radio-frequency waves are a form of electromagnetic energy. They also transfer energy directly into materials, primarily by the interaction of their time-varying electric fields with molecules. Radio-frequency waves may be applied by connecting a radio-frequency alternating current to a pair of electrodes. Between the two electrodes an alternating radio-frequency electromagnetic field having a time-varying electric field component is established. When objects are placed between the electrodes in the time-varying electric field, the time-varying electric field partially or completely penetrates the object and heats it.

Heat is produced when the time-varying electric field accelerates ions and electrons which collide with molecules. Heat also is produced because the time-varying electric field causes molecules, and particularly those with a relatively high electric dipole moment, to rotate back and forth as a result of the torque placed upon them by the time-varying electric field. Most large molecules, or molecules with evenly distributed charge, have relatively low or nonexistent dipole moments and are not very much affected by the radio-frequency time-varying electric field. Small molecules, in particular with polar groups, have relatively large electric dipole moments and thus have relatively large torques exerted upon them by the time-varying electric field. In particular, highly polar molecules, like water, experience relatively large torques and as a result are rotated by the time-varying electric field, thereby transferring mechanical energy to their surroundings as internal energy or heat. Lower frequency time-varying electric fields penetrate deeply and heat objects more evenly. Relatively high frequency time-varying electric fields do not penetrate as deeply, but heat more rapidly the portions of objects they interact with.

It should be noted that a time-varying electric field is always accompanied by a time-varying magnetic field, except where destructive cancellation occurs with interference patterns. For most materials being considered here, the principal heating mechanism arises from the electric fields. These fields can cause both ohmic heating via induced ionic currents and dielectric heating via molecular stressing from the internal electric fields. For very moist materials, the presence of the accompanying time-varying magnetic field can also induce eddy-currents which can also heat the material. Also, some type of combined effect of magnetic fields and heat may occur. While the ensuing discussion is presented in context of an electric field effect, it should be understood that the effects of accompanying time-varying magnetic field are defined here for simplification as part of the electric field phenomena.

Because different materials are composed of different types of molecules with differing electric dipoles, they heat at different rates when exposed to a given time-varying electric field. For example, plastics, which are formed of very large polymer molecules, are not heated by time-varying electric fields as rapidly as water. Metal objects may or may not be easily heated when exposed to time varying electric fields either in the radio-frequency or microwave region. The high conductivity of the metal objects tends to short out the electric fields and rescatter them. As a consequence, there are many conditions where metal objects are difficult to heat, as exemplified by the metal liner of the interior microwave ovens. On the other hand, such time-varying fields can also induce substantial currents which flow on the outside of the metal objects. Under certain circumstances heating effects will occur on the surface of the metal object which, in the case of a small needle, the heat is readily diffused into the interior. In addition, the presence of long, thin metal objects in an electric field causes enhancement of the electric field intensity near the ends of the metal objects and a diminution or shadowing of the fields near the middle. Thus, if the electric field is parallel to the axis of the metal object, strong electric fields will exist near the tips and weak electric fields will exist near the center of the rod or needle. Such field enhancements can lead to arcing and possible fires. In addition, the field suppression or shadowing of such metal objects is also an unwanted feature if the presence of a single electric field vector is relied upon in its entirety to provide the sterilization. The failure of the radio-frequency electromagnetic field to penetrate the object causing surface heating only, or the opposite failure of the materials to absorb the electric field energy, causes uneven heating of the medical waste. The uneven heating is exacerbated because the medical waste usually comprises mixed materials which are difficult to heat effectively using radio-frequency energy due to the presence of areas of high field absorption, such as are due to metals and concomitant shadowing and cold spots. In addition, similar but less pronounced absorption effects are found with water molecules. Thus, when heterogeneous or mixed medical wastes have wet and dry portions, it may be seen that only the wet portions of such material would be heated. Mixed loads such as hospital wastes were considered impossible to disinfect by radio-frequency energy because the waste contains a wide variety of materials, each having different dielectric properties. A great concern was that the presence of a sufficient number of metallic sharps would lead to arcing, causing ignition of the accompanying dry wastes. Another concern was that even if fire was not started, the differential energy absorption of fluids and sharps would leave dry objects undisinfected.

In fact, other attempts to kill microorganisms with radio-frequency energy have been considered unsuccessful. In his 1980 review, "Effects Of Microwave Irradiation On Microorganisms", *Advances in Applied Microbiology* 26:129-45, Chipley cites an experiment of applying radio-frequency energy to bacteria and viruses which grow on tobacco. The experiment found no effect of the radio-frequency energy on the bacteria and viruses. In another study of radio-frequency energy on contaminated liquid food, there was no showing of "selective killing effect" except when ethanol was added.

In the same review, Chipley cited numerous tests of microwaves on microorganisms and concluded that "results of tests for viability of *B. subtilis* spores also showed identical death curves compared with those obtained by conventional heat." On the other hand, however, Chipley cites several references which support the view that microwave irradiation has collateral thermal and nonthermal effects. [For example, Culkin and Fung (1975) found that microbial destruction occurred at reduced temperatures and shorter time periods when the material was exposed to microwaves as compared to conventional heating methods. Wayland et al., 1977 also demonstrated the interdependence of heat and microwaves effects in the studies of spores of *B. subtilis*.

U.S. Pat. No. 2,114,345 to Hayford discloses a radio-frequency applicator with electroscopic control for destroying bacteria in bottled beer and similar products. Hayford teaches an apparatus for sterilizing a series of small objects. The radio-frequency field must be constantly readjusted by the electroscopic control. There is no teaching or suggestion that large scale sterilization of heterogeneous waste could be carried out.

U.S. Pat. No. 3,948,601 to Fraser et al. teaches the indirect use of radio-frequency energy in sterilizing medical and hospital equipment as well as human waste. The reference teaches the use of radio-frequency energy for heating gases, particularly argon, and exciting them so that they ionize into a plasma having a temperature of approximately 100° C. to 500° C. The reference teaches that a cool plasma at a temperature of only 25° C. to 50° C. and very low pressure may effectively sterilize an article. However, sterilization by plasma does not suggest the direct use of radio-frequency waves in sterilization since it is the chemical reactive effect of the plasma which presumably performs the sterilization function rather than the direct or thermal effects of radio-frequency energy on pathogens contained on the material. It may be appreciated that only those portions of the equipment and waste actually contacted by the plasma would be treated.

Reprocessing of the waste, and especially medical waste, is also vital for several reasons. Even if the medical waste has been rendered harmless or innocuous by the destruction of any pathogens associated therewith, there is still the problem of the disposal of the bulk material including the plastics, the sharps, and fibrous material such as gowns, diapers, and the like. The material is relatively bulky and landfills, particularly in many urban areas, have become filled. In addition, older landfills may leak and nonpathogenic but chemically polluting substances may leak into surrounding ground water, causing health hazards. Thus, burying the sterilized medical waste is becoming less attractive. Further, merely burning the sterilized medical waste can pollute the atmosphere and cause acid rain. Current reprocessing technology should be employed to process the disinfected medical waste for effective utilization and proper disposal. What is needed is a method for disinfecting the medical waste and destroying the pathogens thereon and disposing of the disinfected waste in a manner which is harmless to health care workers, waste handlers, and the public at large.

A series of investigations has been undertaken as to sterilization, especially for food. This has resulted in patents or inventions wherein the material to be treated is housed in a microwave transparent container such that the material can be heated at vapor pressures which coexist with temperatures of 120° C. These include Gray U.S. Pat. No. 3,494,723; Nakagawa U.S. Pat. No. 4,808,782; Stenstron U.S. Pat. No. 4,808,783; Landy U.S. Pat. No. 3,215,539; Utosomi U.S. Pat. No. 3,885,915; and Fritz U.S. Pat. No. 4,775,770. All of these patents disclose heating homogeneous material in some form of pouch or pressure container where the material, typically food, is homogeneous. They do not address the special problem considered here where the material is heterogeneous and contains sharps, moist materials and dry materials.

SUMMARY OF THE INVENTION

The present invention provides a method and apparatus for processing medical materials such as medical and veterinary waste and medical products which disinfects the materials by heating them with radio-frequency energy. The invention disinfects bulk medical waste by heating it with a radio-frequency electric field. The medical waste is heterogeneous, that is, it comprises wet and dry materials such as dressings, diapers, tissue and the like and material such as plastic gloves, plastic syringes and the like. The medical waste also contains metal containing sharps as such hypodermic needles, suturing needles, scalpels and the like. The waste is exposed to a radio-frequency electric field having a frequency of in the range of 500 kilohertz to 600 megahertz, preferably about 10 megahertz to about 100 megahertz. The lower frequencies of operation are preferred to assure good depth of penetration of the electric fields into the more moist material. If microwave frequencies are used (above 900 MHz), the depth of penetration is often less than a few centimeters. The depth of penetration is decreased by increasing the moisture content.

While not wishing to be bound by any particular theory, it is noted that the time-varying electric field heats the water on the wet portions and boils off a portion of it. The evaporated water or water vapor apparently travels by convection and diffusion throughout the bag containing the medical waste and may condense on the cooler, dry portions because, other than the metal-containing sharps, dry material has not been heated substantially by the time-varying electric field. It is believed that the condensation of moisture on the formerly dry material gives up heat of vaporization and thereby transfers heat to the previously dry material. It is believed that this transfer of moisture makes the materials relatively homogeneous with respect to water content. This permits all of the material to be rapidly heated volumetrically by the field. The condensed moisture on or in the previously dry material can now absorb energy from the electric field. This generates heat within or on the previously dry material which is now rapidly heated by the field. In one embodiment of the invention, the bags of medical waste are confined within pressure vessels within the electric field and the medical waste is rapidly heated above 90° C. Nevertheless, this temperature kills the pathogens on the waste.

One step of the pressure-vessel method comprises heating the medical materials with radio-frequency energy, possibly within one or more bags housed within a closed container, to raise the internal temperature to about 90° C. In another embodiment, the temperature may be raised to 100° C. The pressure within the bags, if used, increases to a point where the bags will burst thereby interconnecting the fluids among the bags within the container to permit vapor transfer from one bag to another. The heating may then continue to 120° C.

The vapor-containing version of this invention is suitable to treat a wide variety of wet and dry conglomerations of permeable material which must be raised to temperatures below or close to that of the vaporization point of water. The use of radio-frequency heating in such a container creates volumetric heating and reduces the time requirements associated with autoclaving. The invention also is useful for the treatment of certain nonuniform moisture content commodities which are highly permeable, such as breakfast cereals, tobacco, and whole grains, which are highly permeable to gas flow and at the same time often require heating treatments to disinfect the produce, to kill insect infestations and to equalize the moisture contents.

In another embodiment, to implement the vapor-containing version of the process, the materials to be treated may be collected and eventually placed in a plastic bag capable of withstanding temperatures, for about 15 minutes, of just above the vaporization point of water which, in this case for sea-level atmospheric pressure, would be just above 100° C. When the bags are filled, these are sealed and placed in a fiberboard box container. An additional vapor seal such as a fiber reinforced plastic sheet, plastic sheet or cylinder may be applied over a number of boxes which can then be placed in a container for ease of transport through the RF heating facility. The additional vapor seal confines the material up fifteen psig or more.

Thus, by selecting this type of specific packaging, several of the requirements for the successful vapor-containment, disinfection process are realized. First of all, a vapor impermeable barrier is placed around the material. Secondly, the heat capacity of the vapor barrier is small since the wall thickness of the plastic material is quite thin. Thirdly, thermal transfer outside the treatment material is inhibited by the use of the fiberboard box. Such fiberboard boxes are relatively good thermal insulators, owing to the air-sack-like spacing between the inner and outer portions of the fiberbox material. Finally, the outer plastic or fiberglass reinforced vapor prevents intimate contact between the combustible fiberboard or portions of the medical waste with outside air.

One of the embodiments of the invention additionally comprises the step of transferring heated medical waste to a heat-soaking area which maintains the elevated temperature for about 45 minutes. The temperature is maintained in an energy effective and cost efficient fashion in order to provide extra assurance that all pathogens are destroyed by the heat. processed.

However, it may be advantageous in certain situations not to treat the material or waste in a pressure resistant container, but rather the material can be exposed in an unpressurized container to the radio-frequency energy such that the temperature of the material or medical waste is first heated to about 90° C. Further heating to at least 120° C. substantially evaporates all of the water contained in the medical waste. Hence in another embodiment of this invention, to avoid possible underheating effects associated with shadowing through the presence of metallic objects in the waste, the material in the container can be tumbled such that all portions of the material are exposed to all three vector orientations of the electric field.

The tumbling process also ensures exposure of all the material to the electric fields to take advantage of collateral thermal and nonthermal effects which may exist at about 90° C. and may allow complete sterilization to be accomplished without a significant degree of vaporization.

Another embodiment of the invention also comprises steps of further processing the medical waste by presorting the material into recyclable plastic or refuse derived fuel, comminuting or shredding both types of materials, repackaging and shipping to commercial users.

In a still further embodiment of the invention, the medical material, specifically comprising medical and veterinary waste, is received for processing. The waste is then comminuted or shredded to an average linear particle dimension of 1 to 2 inches. If the waste is particularly dry when it is packed in a container for processing, water or foam may be added to the waste. The foam specifically comprises a surfactant such as a detergent mixed with water. The shredding reduces the particle size and reduces the field intensities in any metal materials in the particles in order to reduce the likelihood or intensity of arcing when the shredded material is exposed to the radio-frequency radiation. The container also may be lined with wet material, such as wetted cardboard, to increase its RF absorption.

In most cases, water need not be added to the material as the material contains up to ten percent water by weight. Thus, when the material is heated by the radio-frequency field, water from the wet material is vaporized, transported to the dry material where it condenses, and couples with the radio-frequency radiation to heat the dry material. In the event that water is to be added, it may be added to the container in several ways. First, it may be sprayed on in the form of a misting stream or may be simply be used to soak the shredded material. If large amounts of water, however, are used, the radio-frequency energy may be substantially reflected away from the interior of the container causing the processing time to increase or requiring that higher power equipment be used to obtain reasonable heating times. In order to reduce the amount of reflection, the water may be added in the form of foam which is volume filling, but which has a relatively low average dielectric constant. In experiments which we have performed, foam having a dielectric constant of about 1 to about 10, rather than 80, has been employed, causing only about 10% of the input power at about 10 megahertz to be reflected, rather than about 90% of the input power, as happens with volumes of liquid water. The foam also provides a quenching medium for reducing the likelihood of fires within the container.

One advantage of the above-mentioned pressure vessel which retains vapors up to temperatures of at least 120° C. is obtaining sufficient utilization of the radio-frequency energy by not allowing the water vapor to escape. Thus, energy losses which might occur in a nonpressurized container due to the need to vaporize the water are avoided.

In some versions, the walls of the cavity or belt are heated to a temperature that is comparable to the temperature of the material being processed. As a consequence, in the case of the invention at hand, little or no energy is transferred out of the items to be heated. The purpose of minimizing this transfer is that if the surface is too hot, the material becomes sticky and gummy and thereby eventually clogs the mechanics of the system. On the other hand, if the wall material is significantly lower than that of the material being processed, energy is lost from the material being processed. In the case of wet or moist material where a high energy absorption occurs, this may not be a significant problem, but it can be significant in the case of very dry materials. These have little dielectric absorbing ability and therefore have little capability to simultaneously heat themselves and the adjacent walls. To overcome this, a preferred embodiment of the invention employs the use of peripheral guard heaters along the walls such that the wall temperature assumes approximately the same temperature as that of the material being processed. Alternatively, insulated wall materials may be used which have low thermal conductivity and heat capacity, whereby the heated gases from the material being processed can easily heat the wall so that they can be heated such that the wall temperature can immediately rise to the temperature of the material being The container may be comprised of epoxy fiberglass and is sealed, and may either have a pressurated seal or nonpressurated seal. With the nonpressurated seal, the container will vent moisture at 100° C. With a pressurated seal, the container may be pressurized to about 15 lbs. per square inch above ambient or more, allowing the medical material therein to be heated to 120° C. or more, causing complete disinfection of the material within rapid time.

Before the medical materials are heated, they may also be compacted to allow more material to be heated at any one time and to cause the dielectric material, including the foam and insulating material in the medical waste, to be driven into more intimate contact with any metal therein, causing a reduction in the likelihood of arcing and fires in the medical material when it is heated. Reduction in fires is also achieved in this alternative method by the use of the sealed containers composed of the fire-resistant plastic, which limits the amount of oxygen within the container, to prevent fires from spreading if arcing causes partial combustion of the contents.

In a still further alternative embodiment, the radio-frequency treatment chamber may be a pressurized radio-frequency treatment chamber which can receive relatively low strength plastic containers whose interior pressure may be equilibrated to the pressure within the pressurized radio-frequency chamber. The medical materials then have the radio-frequency energy applied to them to heat them to approximately 120° C. so that the materials are rapidly disinfected by heating due to the applied radio-frequency energy, and possibly also due to the direct electric field effects of the radio-frequency energy on the microorganisms, including viruses, bacteria, and bacterial spores therein.

Therefore, in view of the foregoing, it is a primary object of the present invention to render harmless or disinfect medical materials by heating them with radio-frequency waves. A further object or aspect of the invention is to dispose of disinfected medical and veterinary waste in an environmentally safe manner. Additional objects, advantages, and novel features of the invention will be set forth in part in the description which follows, and in part will become apparent to those skilled in the art upon examination of the following, or may be learned by practice of the invention.

DETAILED DESCRIPTION OF THE PREFERRED EMBODIMENTS

Figure 1:
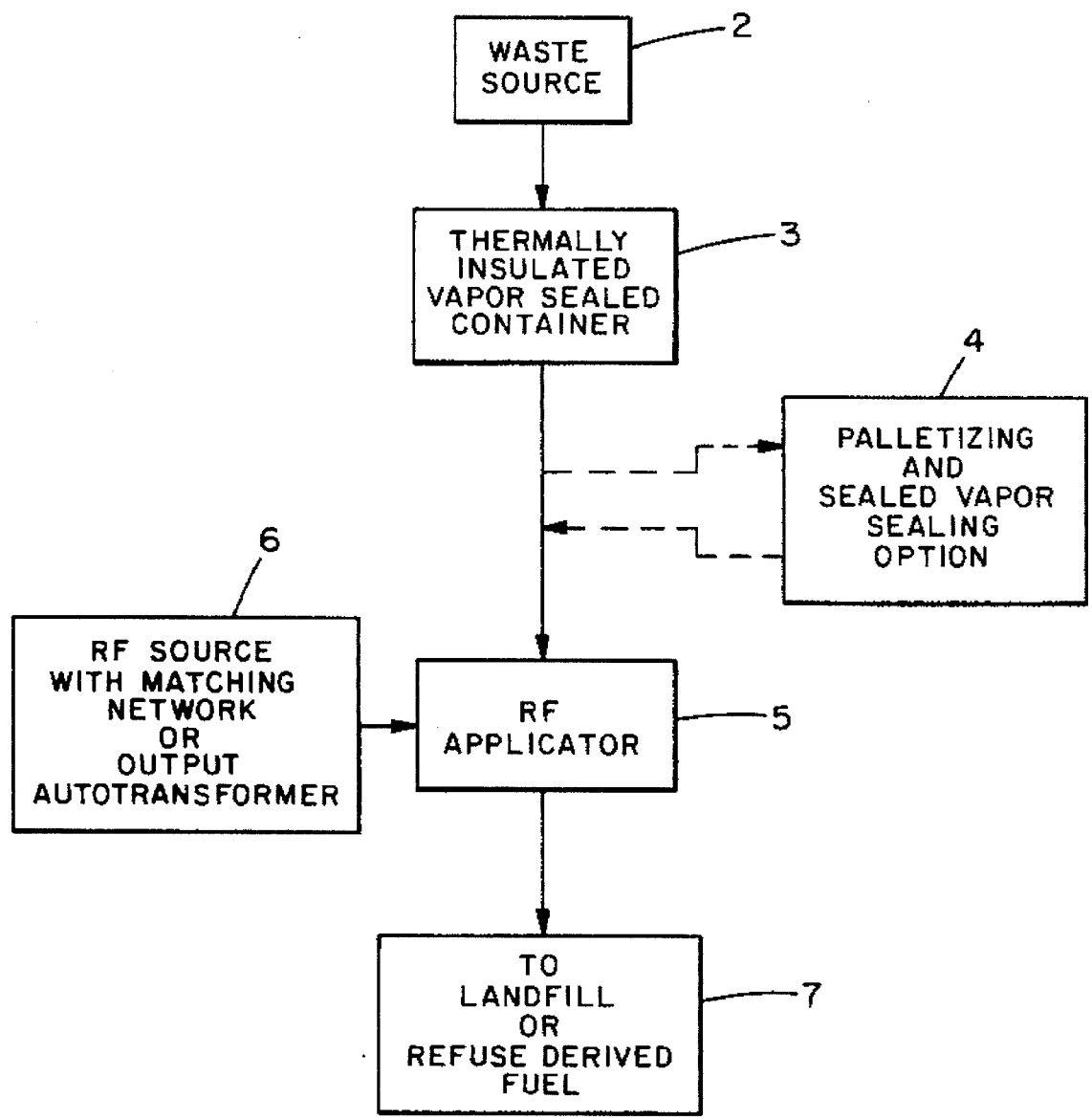
FIG. 1 is a flow diagram of the steps involved in rendering bagged medical waste innocuous by heat treatment with radio-frequency electromagnetic fields.

The method of the instant invention is illustrated in the flow diagram of FIG. 1 and consists of gathering medical waste from a waste source in a step 2 and placing the waste in a thermally insulated vapor sealed container, which may consist of a plastic bag, in a step 3. In a step 4, the vapor sealed container may be placed inside a box and the box loaded on a pallet. The box and pallet are then sealed in a vapor seal comprising a shrink-fit plastic or the like to prevent the escape of moisture from the container during processing. The vapor sealed containers are placed in a radio-frequency field applicator in a step 5 and a radio-frequency power source energizes the applicator to heat the material for a sufficient time to evaporate some of the water therein, transfer the resulting water vapor to dry portions of the material where it condenses and wets providing additional absorption and thereby heats the entire volume of medical waste in a step 6. After heating of the medical waste is completed and the waste is disinfected by heat inactivation of the microorganisms thereon the disinfected medical waste may be converted to a refuse-derived fuel or may be transferred to a landfill in a step 7.

Figure 3:
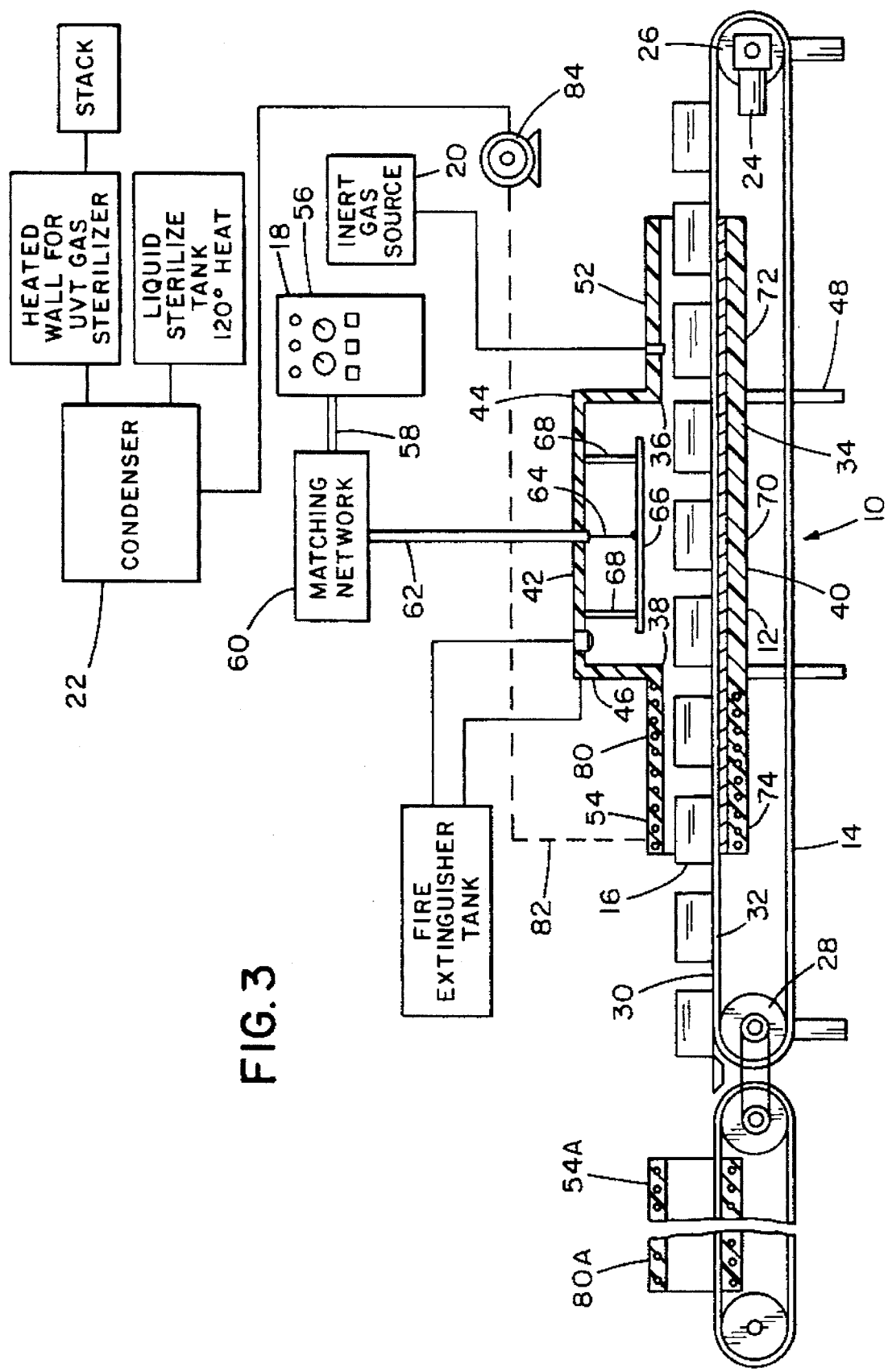
FIG. 3 is a schematic view of a system for continuously disinfecting bagged and boxed medical waste by using radio-frequency energy.

Referring now to the drawings and especially to FIG. 3, an apparatus 10 for continuous waste treatment is generally shown in FIG. 3 and includes a radio-frequency treatment unit 12 and a waste transport system or conveyor 14 for feeding bagged and/or boxed heterogeneous medical waste 16 to the radio-frequency treatment unit 12. A source of radio-frequency energy 18 is connected to the radio-frequency treatment unit 12 to energize it and an effluent handling system 22 is connected to the radio-frequency treatment unit 12 to treat gases and vapors evolved during the heating of the bagged and boxed medical waste 16. Also a source 20 of inert sweep gas, such as nitrogen, is connected to the radio-frequency treatment unit 12 for driving oxygen therefrom to avoid combustion of the medical waste being heated.

The radio-frequency treatment unit 12 includes an applicator or reactor 34 providing a reaction chamber to which radio-frequency energy is applied. The design of the applicator 34 to produce the required electric field and exposure time is of interest. Such applicators may be divided into three basic groups: (1) TEM parallel plate applicators where the wavelength of the excitation frequency is large or comparable to the dimensions of the reactor 34; (2) TE or TM controlled mode applicators where the dimensions of the reactor 34 are comparable to or several times the wavelength of the excitation frequency; and multi-mode TE and TM applicators where the maximum dimension of the reactor 34 is typically 4 or more times the wavelength of the excitation frequency. Typically with the multi-mode TE or TM applicators, the modes are not controlled such that a number of peaks and nulls of the electric field exist within the heating unit, such as exists typically in a microwave oven.

Figure 2A:
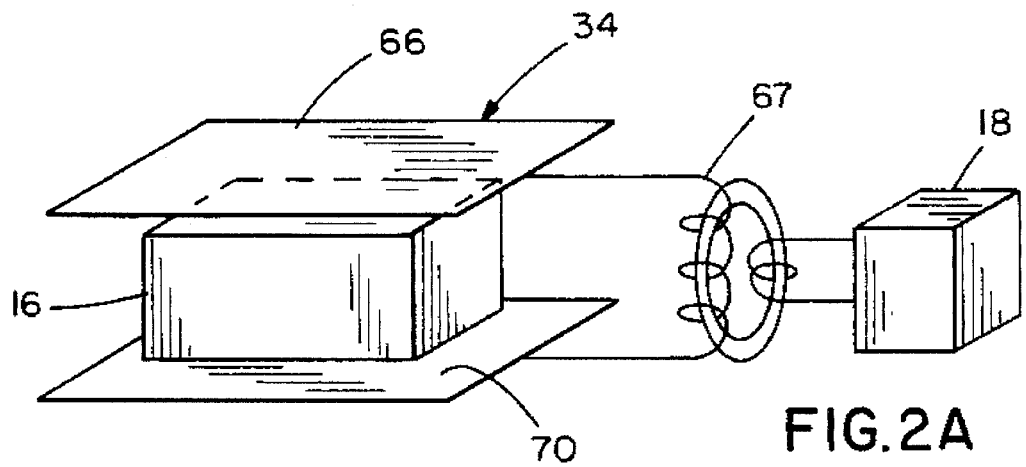
FIGS. 2A, 2B, 2C and 2D are schematic representations of radio-frequency treatment units and radio-frequency energy sources which may be used in the radio-frequency disinfection of infectious medical waste.

FIGS. 2A, 2B, 2C and 2D illustrate the transition from a parallel plate TEM applicator 34 to a controlled limited mode TE or TM applicator. FIG. 2A shows a reactor 34 formed of two parallel plates 66 and 70 with the material 16 placed between the upper and lower plates 66 and 70, respectively. Voltage is applied between the upper and lower plate by means of a tuning coil which is driven from the RF source 18. As long as the wavelength of the applied voltage is large compared to the dimensions of the applicator 34, and the box 16 is well within the extended portions of the metal plates 66, 70, a uniform field can be applied.

Figure 2B:
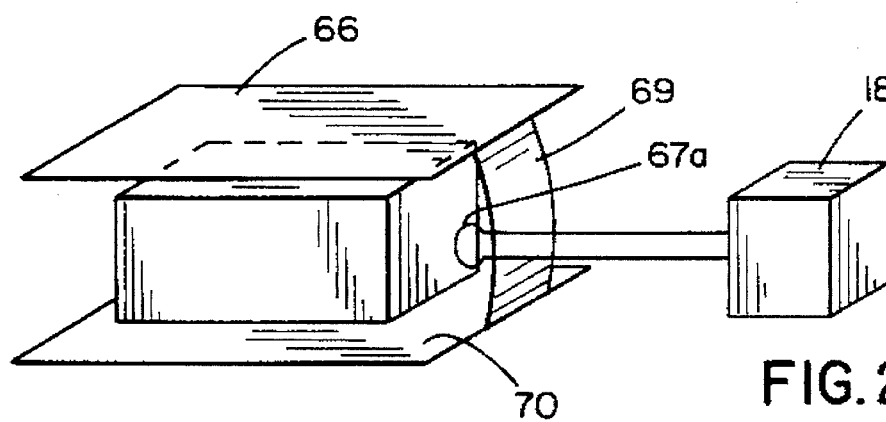
Figure 2C:
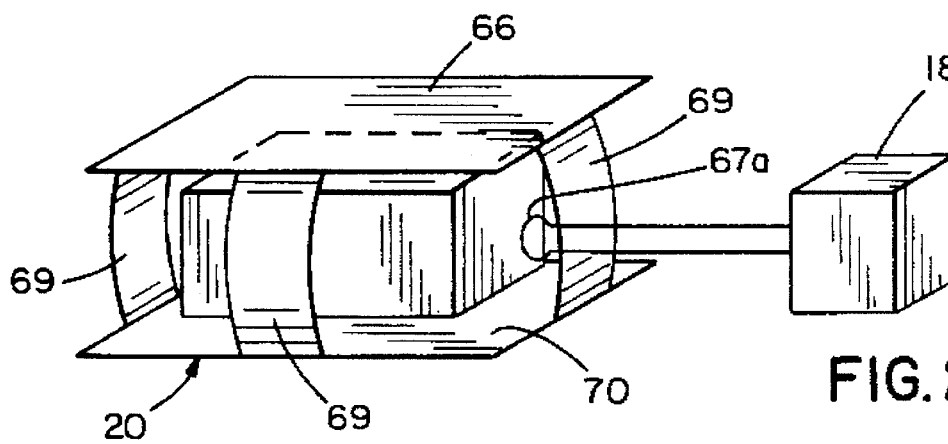
Figure 2D:
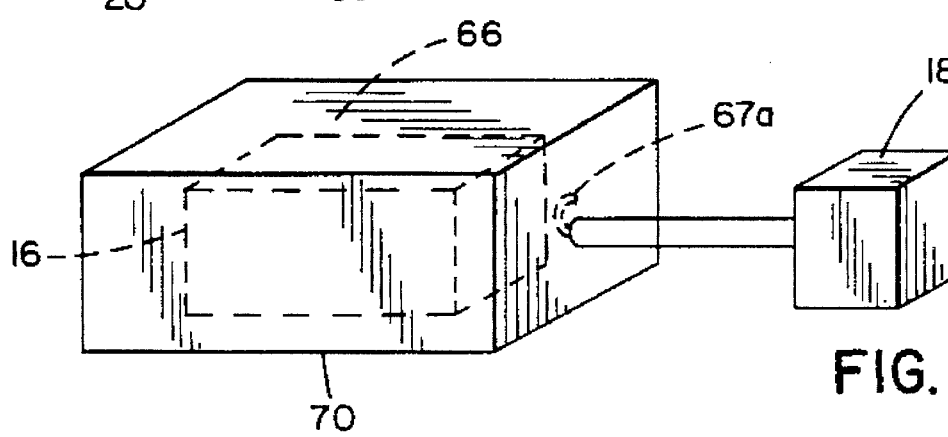

The applicator shown in FIG. 2A is an example of the TEM applicator and is limited to the lower frequencies, and because the dielectric absorption is roughly proportional to the "nth" power of the frequency (where n ranges from 0.3 to 1.0 for frequencies below about 300 MHz) and the square of the electric field strength, substantially higher electric strengths for lower frequencies are required to cause the same heating effect as might be expected for higher frequency operation. Higher frequency operation is possible in a controlled mode heating cavity 34 such as shown in FIG. 2D, which is an example of the controlled mode TE or TM applicator. The transition of the reactor 34 from the embodiment of FIG. 2A to that shown in FIG. 2D is illustrated in FIGS. 2B and 2C. The parallel plates 66, 70 shown in FIG. 2A are resonated with the thin wire series inductance 67. However, by reducing the value of this inductance, higher frequency resonances are possible. Nevertheless, there is an upper limit to the frequency at which this resonance can be made to occur if just a single thin wire solenoidal inductor is employed. To increase the resonant frequency, straps 69 on the sides of the two parallel plates 66, 70 can be employed as shown in FIGS. 2B and 2C, with power applied by way of a launching coil or turn 67. Eventually this arrangement is transformed into the controlled mode TE or TM applicator as shown in FIG. 2D. The controlled mode TE or TM applicator 34 is defined where ½ wavelength is comparable to one of the larger dimensions of the box. This limits the number of permissible modes and allows controlled and uniform heating. In the case of a microwave oven, the dimensions are in the order of 6 to 8 half wavelengths. This results in uncontrolled modes and nonuniform heating.

In another embodiment, as may best be seen in FIG. 3, the waste transport system 14 also includes a conveyor motor 24 which drives an input conveyor drum 26.

An output idler conveyor drum 28 also comprises a portion of the conveyor 14 and a conveyor belt 30 engages both the input driven drum 26 and the output idler drum 28. A portion 32 of the conveyor belt 30 extends through the radio-frequency treatment unit 12 for carrying the containerized medical waste 16 therethrough for treatment.

The radio-frequency treatment unit 12 comprises a radio-frequency chamber 34 having a radio-frequency chamber inlet opening 36 and a radio-frequency chamber outlet opening 38. The radio-frequency treatment unit 12 has a length of 18 meters, a width of 4.5 meters and a height of 3 meters. The radio-frequency chamber 34 comprises a bottom wall 40, a top wall 42, an inlet wall 44, an outlet wall 46, a first side wall 48, and a second side wall 50. Each of the chamber walls is constructed of highly conducting material such as copper or aluminum. Typically 6 millimeter aluminum can be used, which allows the chamber walls to be self-supporting. Also 3 millimeter thick copper could be used in conjunction with additional physical support. The radio-frequency treatment unit 12 also includes an inlet tunnel 52 connected to the inlet wall 44 at the inlet opening 36. The inlet tunnel 52 has a rectangular cross section and is dimensioned to act as a wave guide below cutoff to prevent the radiation of electromagnetic fields from the interior of the radio-frequency chamber 34 to the environment while allowing the containerized medical waste 16 to be carried freely into the radio-frequency chamber 34 by the conveyor belt 30. Likewise, a wave guide below cutoff forms an output tunnel 54 from the outlet 38 at the outlet wall 46 to carry containerized disinfected medical waste 16 out of the vicinity of the radio-frequency treating chamber 34 without allowing radio-frequency energy from the radio-frequency treating chamber 34 to leak into the surroundings.

In order to energize a radio-frequency electromagnetic field and, in particular, the time-varying electric field component thereof, within the radio-frequency treating chamber 34, the radio-frequency energy generator 18 is provided and includes a radio-frequency current generator 56 connected to a coaxial cable 58 for feeding power therethrough. A matching network 60 receives the radio-frequency energy from the coaxial cable 58 to which it is connected. A second coaxial cable 62 is also connected to the matching network 60 to carry the radio-frequency power therefrom. That coaxial cable has a center lead 64 which penetrates the top wall 42 of the radio-frequency chamber 34 and is connected to a vertically movable substantially rectangular conductive exciter plate 66. The outer conductor is connected to the top wall 42 and grounded. The exciter plate 66 is suspended by a plurality of nonconductive ropes 68, preferably nylon or orlon, from the top wall 42 of the radio-frequency chamber 34. This allows the exciter electrode 66 to be moved with respect to the containerized medical waste 16 to provide a spatially uniform, time-varying electric field to heat the containerized medical waste 16 relatively uniformly. A three millimeter thick copper bottom plate 70, which is substantially flush with a pair of bottom plates 72 and 74 of the inlet and outlet wave guide below cutoff tunnels 52 and 54, respectively, comprises the bottom plate of what is in essence a biplate configuration reactor. Typically, the bottom plate 70, as well as the walls 42, 44, 46, 48, 40, and 50 of the radio-frequency chamber 34, are maintained at ground potential while the exciter plate 66 is excited by the radio-frequency energy fed through the coaxial cable 62.

It is particularly important in the practice of the present invention that the exciter plate 66 be movable, as this allows adjustment of the relatively uniform portion of the electric field within the radio-frequency chamber 34. This is important because the size of the containers containing the containerized medical waste 16 may vary from time to time. It is important that when the containers are traveling through the center portion of the radio-frequency heating chamber 34, they be subjected to a substantially spatially uniform time-varying electric field so that the contents thereof are uniformly heated.

Figure 4:
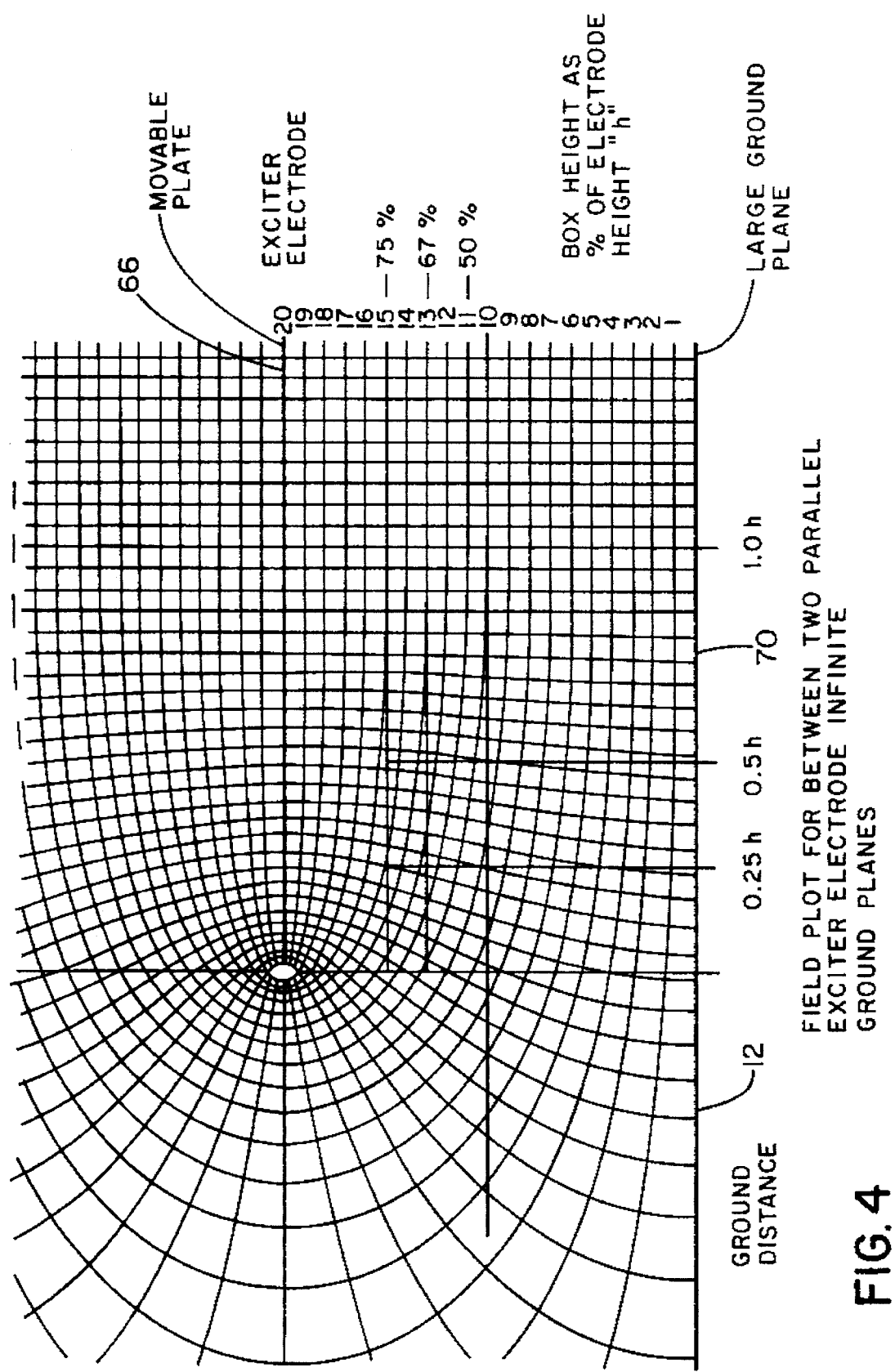
FIG. 4 is a section of a radio-frequency reactor of FIG. 3, showing the electric field vector lines and equipotential lines generated within the radio-frequency treatment unit.
Figure 5:
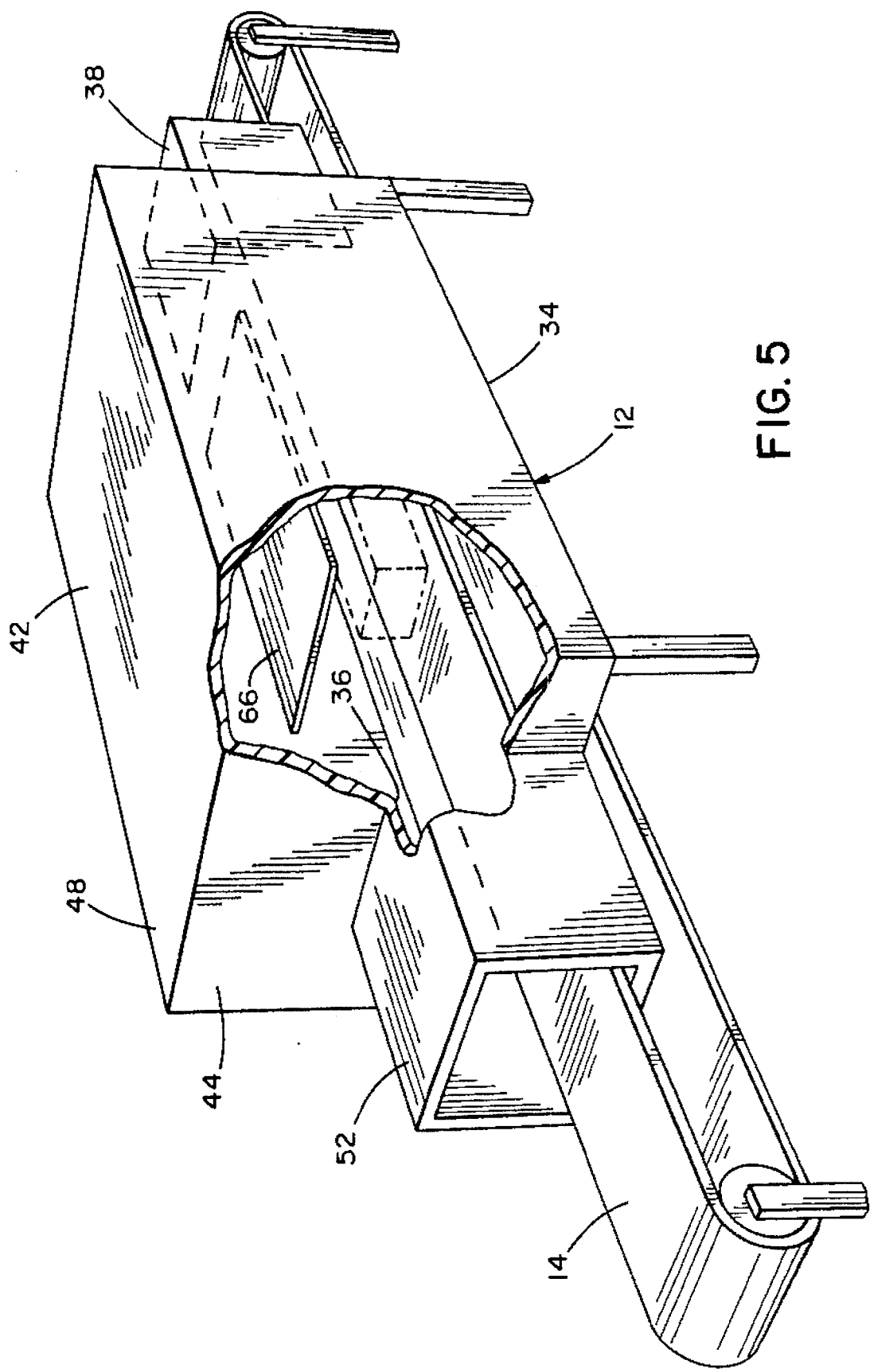
FIG. 5 is an isometric view of the radio-frequency treatment unit of FIG. 3 and a conveyor associated therewith showing details of the orientation of the conveyor with respect to an exciter plate within the reactor and the radio-frequency treatment unit.

In the case of the parallel plate exciter, the dimensions of the box 16 compared with the dimensions of the electrode 66 are important in order to assure reasonably uniform electric field and resultant heating effects. To determine the relationship between the box dimensions and the size of the electrode exciter, the data in FIG. 4 were developed. This shows equi-potential lines (horizontal) coupled with the displacement current lines (near-vertical) for a limited extent exciter electrode 66 centrally located in a large conducting box. The relative electric field at any location can be developed by determining the dimensions of a square at any location and a similar square in the uniform region (far right) and dividing the maximum dimensions of this uniform field square by a similar dimension of the square at the desired location.

It can be seen therefore, if the guard distance, that is the distance from the edge of the box to the downward projection of the edge of the electrode, is equal to the height of the electrode, that very little field distortion occurs and that the electric field in the region to the right of this point is reasonably uniform. Further studies show that if the edge of the box is moved farther to the left, field distortion occurs such that the electric field is significantly less near the ground plane and therefore the material of the box would experience a significantly lower heating rate. Guard distances which are equal to about one-fourth or less than the height of the exciter electrode are relatively unsatisfactory.

On the other hand, it is seen that as the height of the box is increased, the field distortion near the edge of the electrode is such as to contribute excess field intensities, particularly where the height of the box is 75% of that of the exciter electrode and the guard distance is equal to one-quarter of the electrode height. Data taken from this plot are summarized in Table 1. It may be seen that guard distances as little as one-fourth the height of the electrode are acceptable but, on the other hand, the maximum height of the box probably should preferably be no more than 67% of the height of the exciter electrode. The reason for this is that as the box enters from the left going into the right, it encounters increasingly high levels of electric field near the edge of the electrode. As a consequence, excess field intensity can occur there which can lead to potential gradients and arcing phenomena. To ensure against such effects as well as over or under heating, the normalized heating rate during entry wear the top edge of the box should not vary more than 1.5 to 1.0 for the parallel plate type of heater shown in FIG. 3. Where the bulk of the water is not evaporated but rather repositioned, heating ratios of 2.0 to 1.0 can be tolerated. Where the bulk of the water is evaporated and heating is contained beyond the vaporization point, the heating rate variation should be less than 1.5 to 1.0.

TABLE 1

HEATING POTENTIAL ($E^2$) NORMALIZED TO THE HEATING POTENTIAL IN THE UNIFORM FIELD REGION AS A FUNCTION OF THE BOX HEIGHT RELATIVE TO THE HEIGHT OF THE ELECTRODE AND FOR RELATIVE GUARD LENGTHS.

| Dimensions Relative to Electrode Height, h | | Normalized Heating Potential, ($E^2$) | |
|---|---|---|---|
| Box Height | Guard Length | Top of Box | Bottom of Box | Top of Box During Entry |
| 0.5 | 0.5 | 0.92 | 0.96 | 1.0 |
| 0.5 | 0.25 | 0.92 | 0.88 | 1.0 |
| 0.67 | 0.5 | 1.25 | 0.96 | 1.21 |
| 0.67 | 0.25 | 1.10 | 0.88 | 1.21 |
| 0.75 | 0.5 | 1.44 | 0.96 | 1.8 |
| 0.75 | 0.25 | 1.2 | 0.88 | 1.8 |

In the present embodiment, in particular for the type of reactor shown in FIG. 3, a 12 megahertz radio-frequency current generates a 12 megahertz radio-frequency electric field within the radio-frequency chamber 34 to heat the medical waste 16 within the hospital waste containers. It may be appreciated that the hospital or medical waste may comprise a wide variety of waste having many different dielectric constants. For instance, the sharps will include metals in which collected displacement currents will be induced by the time-varying electric field. Very moist materials will also be included, as well as quite dry materials such as gloves and the like. In particular, the moist materials couple well with the radio-frequency field due to the fact that the dipole moments of the water molecules cause the water molecules to have a torque exerted thereon by the electric field when it is unaligned with the dipole moments. This causes the molecules to be moved, in particular rotated by the field. The water molecules then transfer disordered kinetic energy to the materials upon which they are in contact, causing them to be heated.

When the medical waste 16 is first placed in the radio-frequency chamber 34, the wet portions of the medical waste 16 are rapidly heated by the radio-frequency energy, causing water vapor to be evolved therefrom. The water vapor is dispersed by convection and diffusion throughout the bags of hospital waste and condenses on the dry waste therein, due to the fact that the dry waste has been relatively unheated until it comes in contact with water. The condensation of the water vapor on the cooler material transfers heat thereto by giving up heat of vaporization. More importantly, however, the condensed vapor wets the formerly dry material whereby the water is volumetrically heated by the time-varying electric field, thereby generating thermal energy in the previously dry waste and causing the waste within the container to be substantially uniformly volumetrically heated. Since the frequency of the time-varying electric field is selected to be 12 megahertz, or, in the alternative 64 megahertz, the electric field penetrates well into typical waste bags, and the entire volume of medical waste within the bags is substantially uniformly heated once the water is dispersed, allowing the waste to be rapidly heated. Once a minimum temperature of about 90° C. is reached, virtually all pathogenic organisms are all destroyed by the heat, and the waste is disinfected.

In one embodiment of the invention, as shown in FIG. 3, the exit tunnel 54 is lined with electric resistance heaters 80, which are means for heat soaking the medical waste, if a further margin of safety is desired. As the containerized medical waste 16 passes through the exit tunnel 54, the electrical resistance heaters 80 transfer sufficient heat energy via radiation to prevent heat loss from the waste 16. This heat is not sufficient to raise the temperature of boxes 16 further, but it is only sufficient to maintain the temperature of the boxes at the exit. As a result, the exit tunnel 54 in combination with a similar tunnel 54a of much longer length will provide a means for heat soaking the medical wastes over the appropriate period of time. This can be done with a relatively low power consumption in order to hold the medical waste at the desired temperature for up to approximately 45 minutes. In addition, such a heating tunnel in combination with the RF source heating method provides a means to heat the medical waste in a controlled manner such that combustion does not occur and the plastic does not melt or partially pyrolyze. It would, of course, be difficult, if not impossible, to use such electric resistance heaters or other infrared radiative heaters solely to heat bulky materials like the hospital waste from ambient temperature due to the fact that infrared heaters provide essentially surface and not volumetric heating. That is, in accordance with the present invention, the waste is first heated volumetrically to the desired temperature and held at that temperature by surface heating. If the surface is maintained at the desired temperature, the interior cannot cool.

Doors may be provided at the distal ends of the inlet wave guide below cutoff 52 and the outlet wave guide below cutoff 54 as well as the heat soak entrance and exit to trap gases generated by the heating within the unit. These gases might, like the contents of the medical waste containers 16, be combustible. As a result, the inert gas system 20 floods the radio-frequency heating chamber 34 as well as the inlet tunnel 52 and the outlet tunnel 54 with nitrogen. The flow is a counter flow in the inlet tunnel 52 keeping oxygen out of the system in order to prevent fires. The nitrogen flush also provides other important features to the invention. Since the injection point for the nitrogen flush is near the inlet tunnel 52, or actually on it, the relatively cool nitrogen enters the radio-frequency treating area at approximately the same temperature as the waste 16. Nitrogen is carried in the same direction as the waste 16 and is heated thereby by conduction, radiation and convection from the heated medical waste 16. As a result, an effective temperature ramp is provided from the inlet portion of the radio-frequency heating chamber 34 to the outlet portion by the flowing of the gas in combination with the gradual heating. Due to the fact that the gas flows in the direction in which the temperature is increasing, refluxing of any vapors released from the containerized medical waste 16 is prevented to the cooler input hospital waste by the directed flow of the nitrogen gas and thus prevents condensation on the cooler exterior of the containers, which could inhibit volumetric heating. The nitrogen gas also operates as a sweep gas and carries effluents out through an effluent exit port 82 which comprises a portion of the inert gas system 20. The effluent exit port 82 is connected to a blower 84 which is connected to the effluent treatment system 22.

Figure 12:
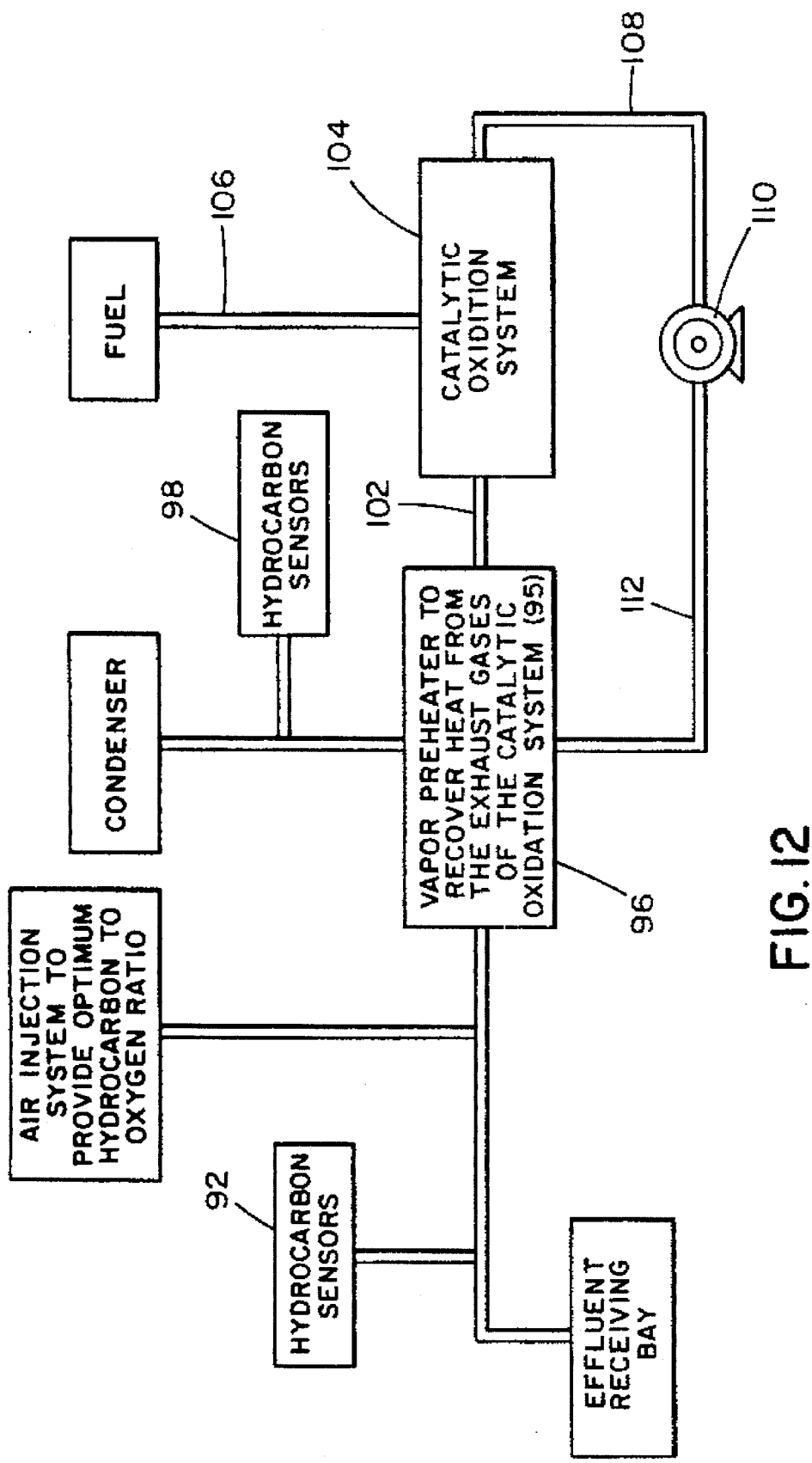
FIG. 12 is a diagrammatic view of the vapor treatment system associated with the apparatus shown in FIGS. 3 and 8.

The effluent treatment system 22, as may best be seen in FIG. 12, processes the effluents evolved in the heating of the infectious medical waste. These effluents essentially consist of steam, air and inert gases, such as the nitrogen sweep gas, as well as some hydrocarbons generated during heating of the waste and possibly pathogens that might have been released during the waste processing. Under normal conditions, though, all of the pathogens would be inactivated or destroyed by the radio-frequency heating. The effluent exits through the duct from the radio-frequency heating chamber 34 and passes a hydrocarbon sensor 92 connected to the duct 82 for determining whether hydrocarbons are present. If hydrocarbons are present in excess of a predetermined value, an air injection system 94 injects air into the effluent gas stream so that a combustible mixture of air and hydrocarbons, as well as inert gases, is fed to a vapor preheater 96. The vapor preheater is a heat exchanger fed with exhaust gases from downstream equipment. A hydrocarbon sensor 98 is connected to a condenser duct 100 adapted to receive an inlet from the condenser. The gases are then fed through a duct 102 to a catalytic oxidation system 104 which may be purchased from Allied Signal UOP or other commercial suppliers. The catalytic oxidation system receives fuel such as propane or natural gas, if needed, via a fuel delivery line 106. The catalytic oxidizer also includes a catalyst, such as Torvex catalyst available from Englehart, for the oxidation of hydrocarbons into carbon dioxide and water. The oxidizable components are oxidized by contact with the catalytic oxidizer and resulting hot combustion products are fed through a combustion output line 108 to a blower 110 which directs the hot combustion products through a hot gas output line 112 into the heat exchanger 96 to conserve heat energy by transforming heat from the hot combustion products before they are vented to the environment to the effluent gases in the input duct. The combustion products are then vented through the output duct 100 to the environment. The hydrocarbon sensor 98 will signal an alarm if unburnt hydrocarbons are passing through the output duct 100, causing a system shutdown to allow correction or alteration of the system parameters to ensure complete combustion of all combustible effluents. The combustion of the combustible effluents also destroys any pathogens which may be trapped therein and which had remained active before combustion.

Figure 13:
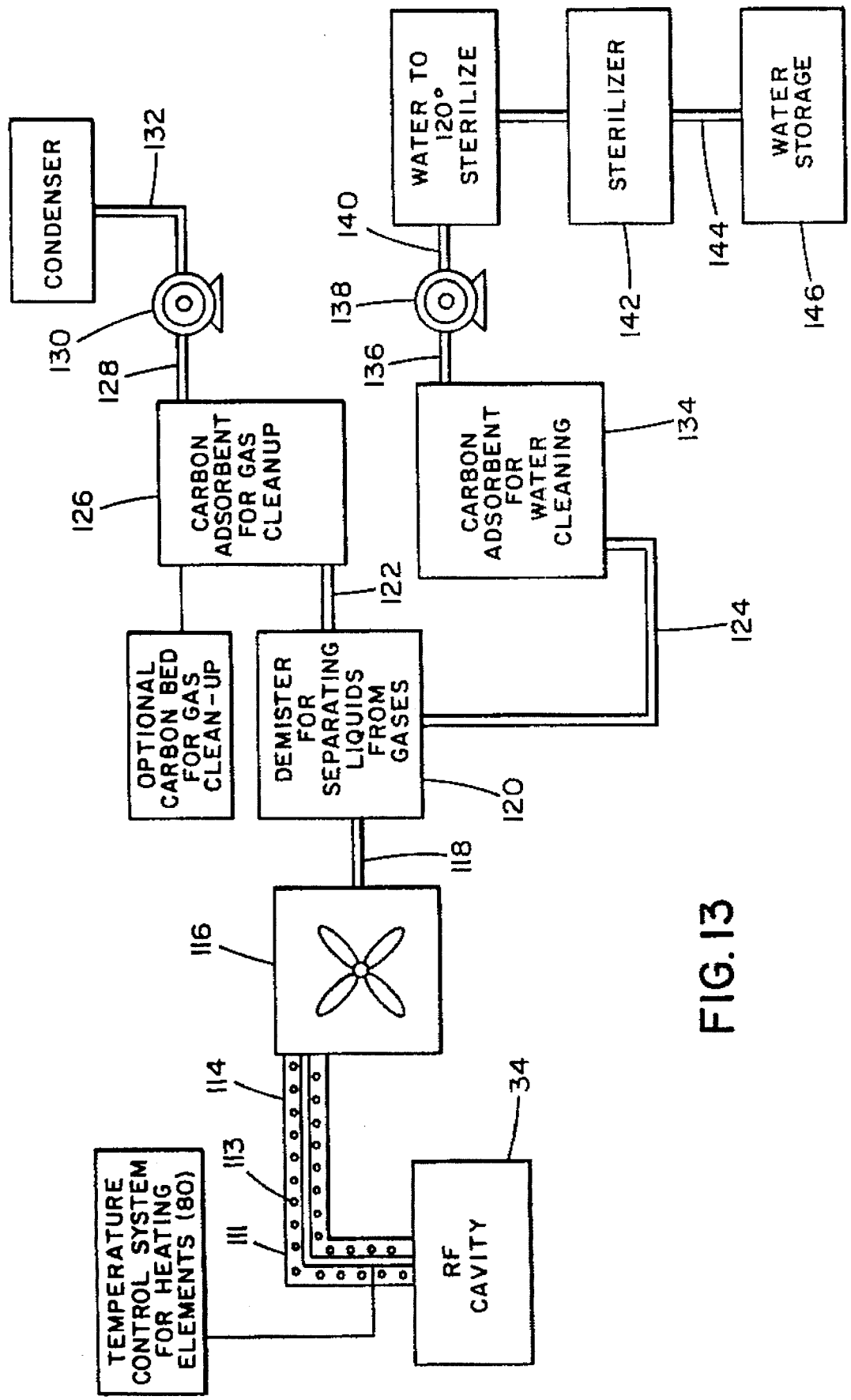
FIG. 13 is a diagrammatic representation of an alternative vapor treatment system employing condensation and waste treatment.

In an alternative system, the radio-frequency chamber 34, as may best be seen in FIG. 13, is connected to an effluent output line 111 having electrical resistance heating elements 113 wrapped thereabout to maintain a high temperature of the output effluent, thereby preventing any heavy fractions from condensing within the duct 111 and also disinfecting the effluents. Thermal insulation 114 is also wound about the heating elements 113 to prevent excessive heat loss from the electrical heating elements and also to prevent condensation of heavy fractions within the duct 111. An air cooled vapor cooling system 116, which in the alternative may be water cooled, causes condensation of heavy fractions into liquid which may then be passed by a duct 18 to a demister 120. The demister 120 separates any remaining gas flowing through the duct 118 into a gaseous fraction which is fed on a gas line 122, and a liquid fraction fed via a liquid line 124. A carbon adsorbent system 126 receives the gas from the line 122 and vents any inert gases left over through a line 128 which is connected to a venting blower 130. The venting blower 130 feeds the remaining inert cleaned gases through an output duct 132 to the environment. Similarly, the liquids are fed via the duct 124 to a liquid adsorbent system 134 which is filled with a commercially available adsorbent material for water cleaning, such as Filtrasorb from Calgon. As an added precaution, clean water is then fed via duct 136 to a pump 138 which passes the clean water through a pipe 140 to a sterilizer 142 which heats the water to 90° C. for sterilization. The sterilized water is fed via a duct 144 to a receiving container 146 which receives and stores it. The sterilized water may then be disposed of in an appropriate manner.

Figure 8:
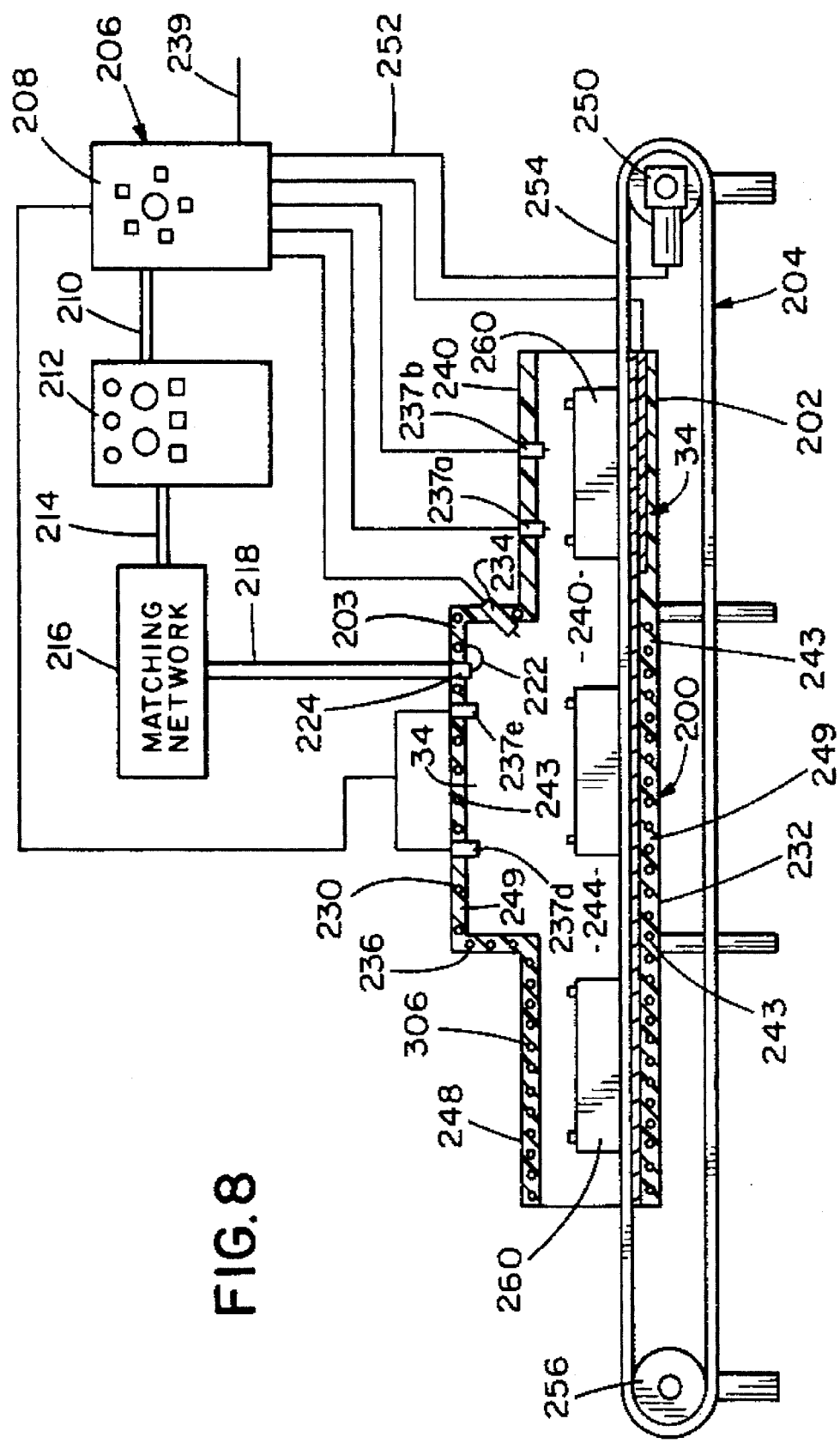
FIG. 8 is a schematic view of a semicontinuous waste disinfect system employing the radio-frequency treatment unit illustrated in FIGS. 6A, 6B and 6C.

As may best be seen in FIG. 8, an alternative semicontinuous waste system 200 is shown therein, utilizing the radio-frequency system shown in FIG. 6. The semicontinuous waste disinfection system 200 includes a radio-frequency waste treater 202 and a waste transport system 204. A radio-frequency energy generator 206 is coupled to the radio-frequency waste treating reactor 34. In operation, the radio-frequency energy generator 206, which includes a control system 208 connected via a cable 210 to a radio-frequency power source 212, generates radio-frequency energy in response to control signals from the control 208 and feeds the radio-frequency energy via a cable 214 to a matching network 216. The matching network 216 has a power delivery cable 218 connected to it which has an inner conductor 220 terminating at a field exciter 222 of a loop type or other suitable type. A dielectric plug 224 terminates an end of an insulating jacket 226 of the coaxial cable and mates with an upper wall 203 of the radio-frequency waste treating reactor 34. The radio-frequency waste treating reactor 202 also includes a bottom wall 232, an inlet wall 234, an outlet wall 236, and a pair side walls, one of which is shown as a first side wall 238. Coupled to the treatment chamber is an inlet wave guide below cutoff tunnel 240 which is substantially rectangular in cross section, connected at an inlet 242 to the reactor 34. The reactor 34 also includes an outlet 244 formed in the wall 236 to which is conducted an outlet tunnel 248 which comprises a radio-frequency wave guide below cutoff. The system may also include an inert gas source as well as an effluent handling system as shown in FIG. 3, although for simplicity such are not shown in FIG. 8.

The conveyor system or waste transport system 204 includes an electric motor 250 controlled by signals carried on a cable 252 from the control 208. The motor 250 drives an input drum 252 of the conveyor system which in turn drive a conveyor belt 254. An output drum 256 also engages the belt 254 in a conventional fashion.

Figure 10:
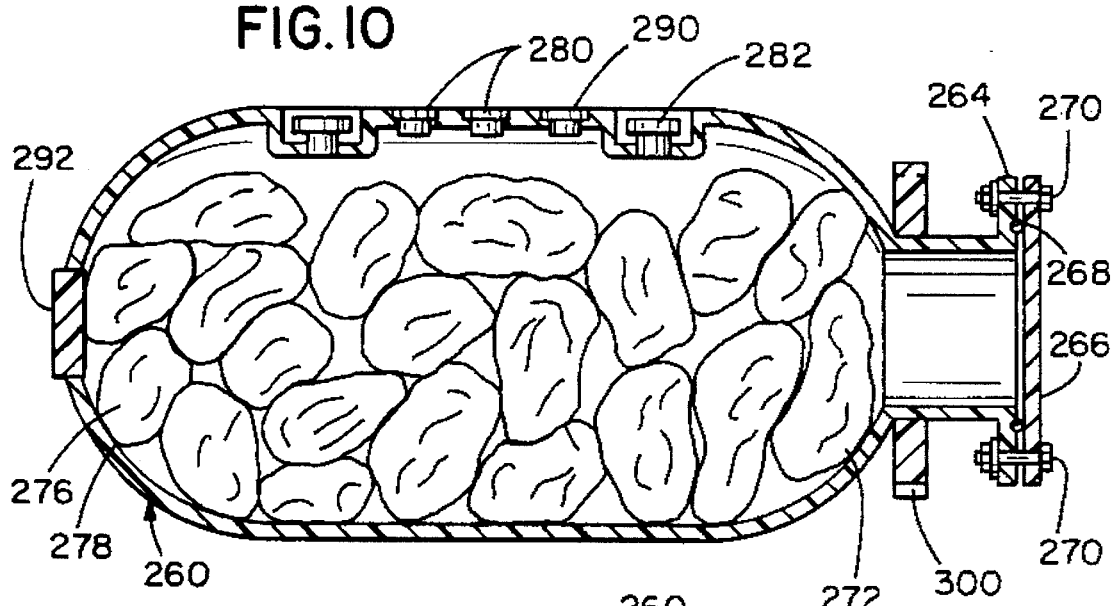
FIG. 10 is an elevational view, shown partly in section, of a pressure vessel for holding bagged medical waste for placement inside the radio-frequency reactor of the apparatus of the present invention.
Figure 11A:
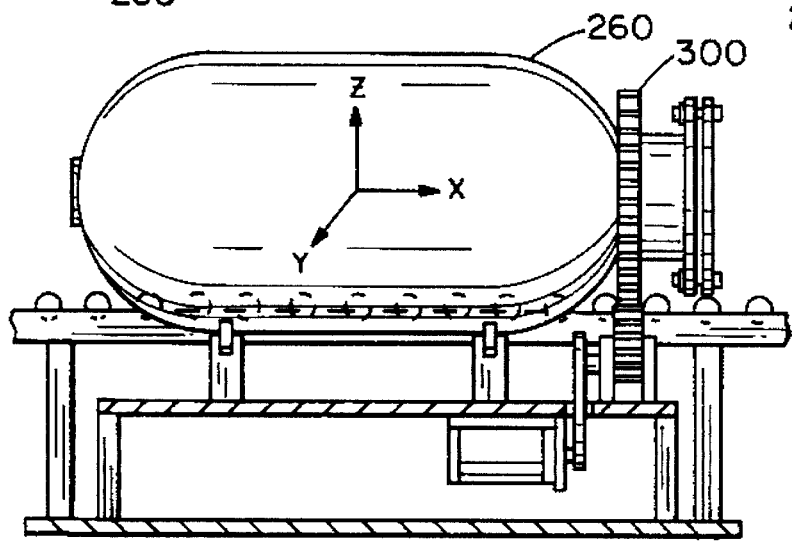
FIGS. 11A and 11B show side and end elevational views of the pressure vessel of FIG. 10 and the mounting and driving apparatus therefor.
Figure 11B:
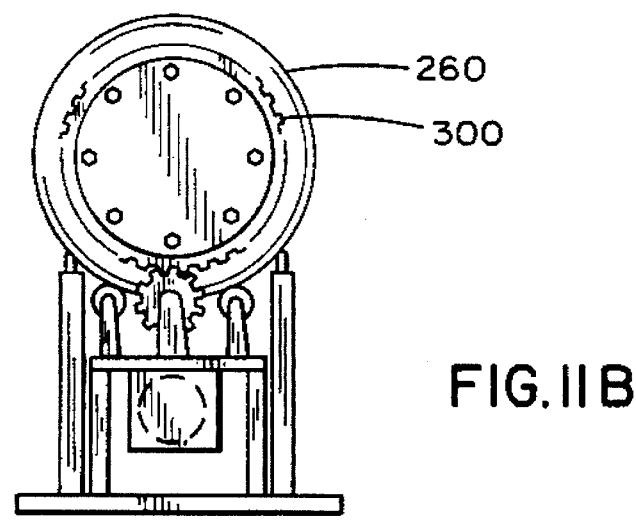

Pressure vessels 260 of the type which may best be seen in FIGS. 10, 11A, and 11B, are carried by the conveyor belt 254 through the inlet tunnel 240 into the radio-frequency reactor 34. The pressure vessels 260 are substantially cylindrical in shape and include an inlet 262 terminating in a flange assembly 264 which receives a closure cap 266. The closure cap 266 seats against an O-ring or gasket 268 for a gas tight seal therewith. The O-ring 268 is also trapped against the flange 264. The cap 266 is held in compressive engagement with the O-ring by a plurality of bolts 270. The pressure vessel 260 includes a wall 272 which may either be completely transparent to radiofrequency radiation, or be deliberately absorbent to heat the wall by the radio-frequency energy such that the wall temperature approximates that of the material being heated. Alternatively, the interior portion of the wall of the container may be thermally insulating to achieve the same purpose. The pressure vessel 260 is preferably made using fiberglass reinforced high temperature epoxies or equivalent plastic material to withstand the temperatures and pressures needed for disinfection. A plurality of waste bags 276 are held in the interior 278 of the pressure vessel 260 for heating by the radio-frequency energy as was set forth above.

A plurality of thermocouple openings 280 are provided in an upper portion of the vessel so that, if desired, temperature readings may be made of the interior of the vessel 260 to assure a minimum of 90° C. A pair of pressure relief valves 282 are also included. The pressure relief valves are rated at about 15 psi, that is, they remain closed until the internal pressure of the vessel 260 exceeds the external pressure by 15 pounds per square inch. This allows vapor to be contained even if the medical waste 16 is heated above 100° C., the boiling point of water at atmospheric pressure. It also allows the waste or medical materials to be heated to 120° C. without vaporizing most of the water within the bags. The release valves 282 are provided in order to protect the operators of the system from overpressure within the pressure vessels 260. Should it be necessary to inject additional water into the pressure vessel 260, a water injection port 288 is provided in the wall of the vessel. A rupture disk 290 is also provided in the vessel 260 to prevent excessive buildup of pressure in the event of failure of the pressure release valves 282. An optional disinfected waste port 292 is provided as an aid for pushing medical waste from the pressure vessel 260 following disinfection with the radio-frequency energy.

The pressure vessel 260 also includes gear cogs 300 arranged around the neck 262 of the inlet of the pressure vessel 260. When the pressure vessel 260 is transported into the radio-frequency heating chamber 34, the drive gear box 304 and mounting assembly 301 are normally below the bottom surface 232 of the reactor 34. To rotate the vessel, the drive gear 304 and the mounting assembly 301 are raised so that the drive gear 304 engages the cog 300 to rotate the pressure vessel so that all containerized medical waste within the pressure vessel 260 is exposed to all three time-varying vectors of the electromagnetic field to further ensure complete electric field exposure and uniform heating.

In an alternative embodiment the pressure relief valves can be set to relieve the pressure at nearly atmospheric levels. The pressure vessel thus can be used both as a waste bag container for transportation through the system and to contain vapors for vapor transfer for condensation on dry materials.

In the event that the heating is to be taken above the vaporization point at atmospheric pressure, then it is important that the large pressure vessel also be rotated to eliminate the possibility of shaded areas, as previously discussed. Thus, by this method, all parts of the waste material are exposed to substantial levels of electric fields with a resultant possibility of achieving lower temperature disinfection by the combined or collateral effects of temperature and electric fields. In practice, the material in the temperature vessel first is heated to the vaporization point of water as in the case for the system shown in FIG. 3. The dry, relatively poorly absorbing material receives water vapor from the moist medical material and thereby becomes more absorbing to realize an almost equal temperature rise of the wet and dry medical material within the bags. At this point a minimum temperature in the bags of 90° C. may be realized. Then the bags and the boxes are removed through the exit tunnel and heat soaking arrangement as previously described for the 90° C. or more heat soaking system, except that the heat soaking temperature in this case of 100° C. may be preferred.

Alternatively, it may be desirable to further heat the material at atmospheric pressure to temperatures of about 100° C. or 120° C. This may be done by further application of the time varying electric fields such that the material is dehydrated nearly completely and a minimum temperature of 100° C. or 120° C. is realized through dielectric heating.

In many cases, especially if pressurization at near atmospheric levels is employed and if heating beyond the vaporization temperature of the dry medical material is required, the total energy or "dose" applied to the medical waste must be controlled. Energy should be sufficient to accomplish the desired final temperature with some additional safety margin. This may result in some of the medical material being overheated beyond the desired final temperature of approximately 120° C. However, too little energy can result in underheating some portions of the medical material and too much energy can result in excessive energy consumption along with partial or complete pyrolysis of the medical waste. Excessive waste also generates noxious gases and thereby burdens the effluent treatment system.

To mitigate these problems, as shown in FIG. 8 sensors 237a and 238b are used to determine the moisture content and/or the presence of sharps. Previously the material may have been weighed and the weight data supplied to the control unit 208 via a cable 239. The control unit 208 then programs the exposure level and controls this via the electric field sensor 234 and the duration of the exposure by sequentially activating the belt 254 via a line 252 and a motor 250. A sensor 237d remotely monitors the temperature of the material in the vessel 260 by monitoring the infrared or longer wavelength electromagnetic emissions from the material being heated. The sensor 237e monitors the gaseous effluent so as to limit excessive pyrolysis.

Additional wall insulation and/or wall heating may also be employed to suppress heat losses due to convection and diffusion. This is especially desirable if heating above the vaporization temperature is needed. Additional wall and panel insulation 241 along with a wall and a panel heater 343 may be employed. The wall and panel heater 343 is also controlled by the control system 208.

For those cases where heating above the vaporization point of water is employed, it is especially important that the chamber be filled with an inert gas such as nitrogen. The means for the injecting the nitrogen in and keeping the oxygen out are described for the system shown in FIG. 3. For the semicontinuous system shown in FIG. 8, less care is needed in controlling the direction of sweep gases. However, if a continuous version of FIG. 8 is employed, the direction of sweep gases should be from the cooler material to the hotter material as discussed in the embodiment shown in FIG. 3.

The pressure vessel may then be carried, after treatment by the radio-frequency energy, to the outlet tunnel 248 where electrical resistance heaters 306 provide heat soaking to the pressure vessel 260, holding it at the desired temperature for a specified period of time in order to provide extra assurance of the destruction of pathogens in the infectious medical waste.

Figure 6A:
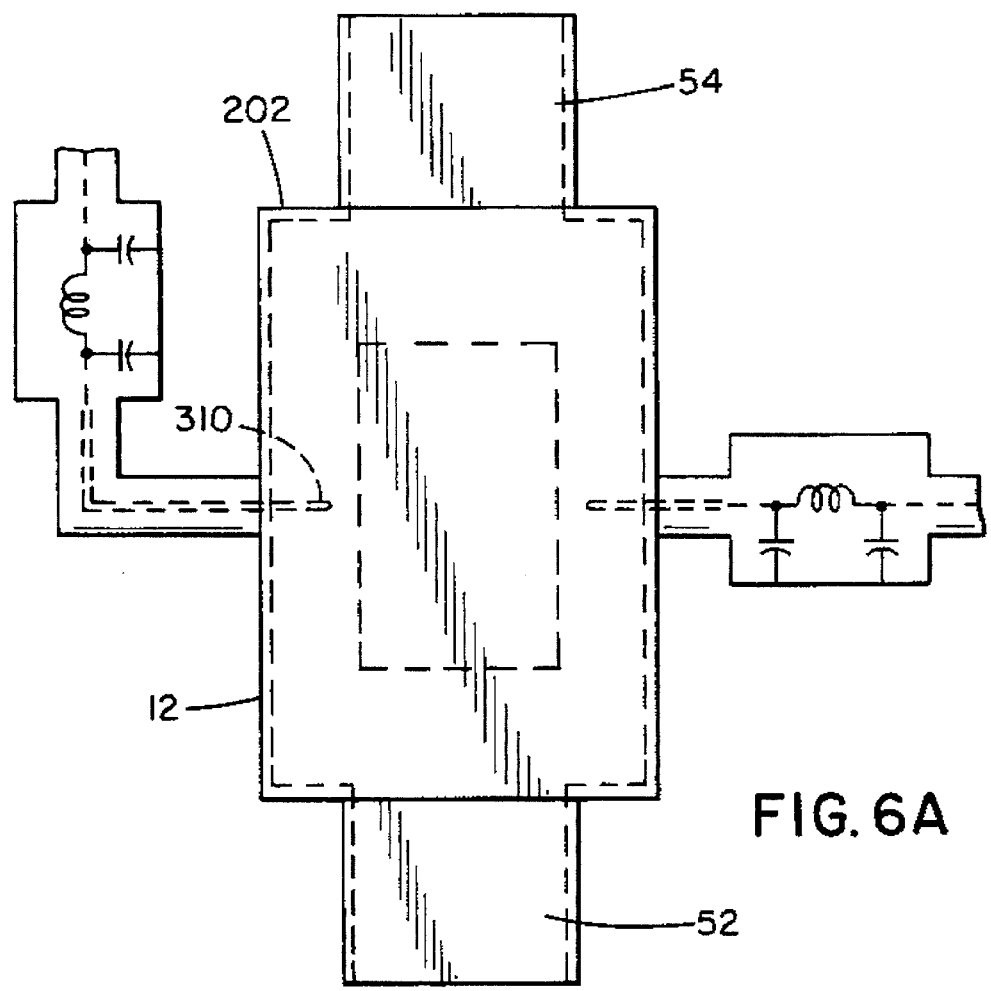
FIGS. 6A, 6B and 6C are plan and front side elevational views of a different type of radio-frequency treatment unit which can be used without the exciter plate, the top and bottom of the shielded cavity serving as termination points for the electric fields, thereby simplifying the cavity design and permitting operation at higher frequencies.
Figure 6B:
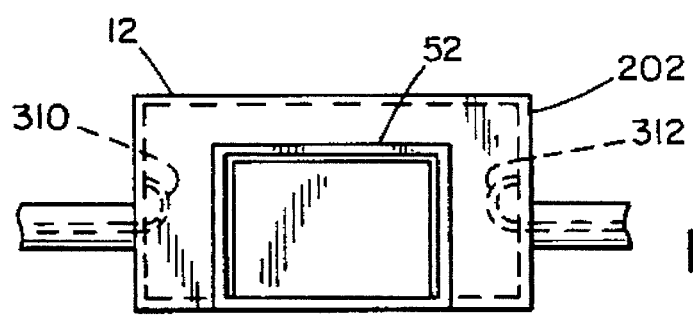
Figure 6C:
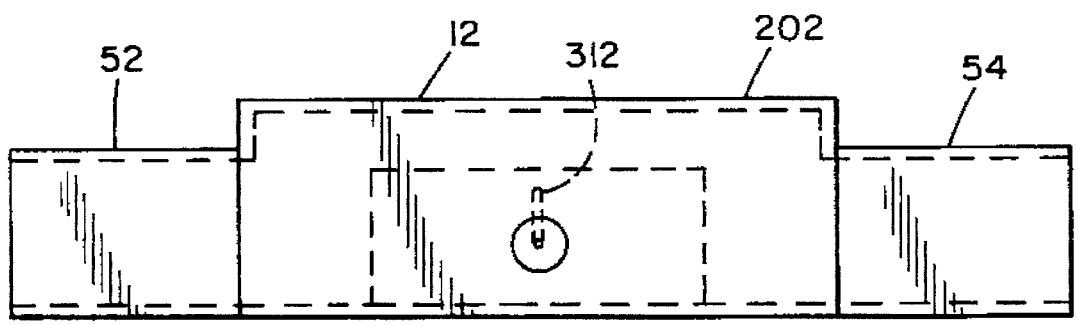
Figure 7A:
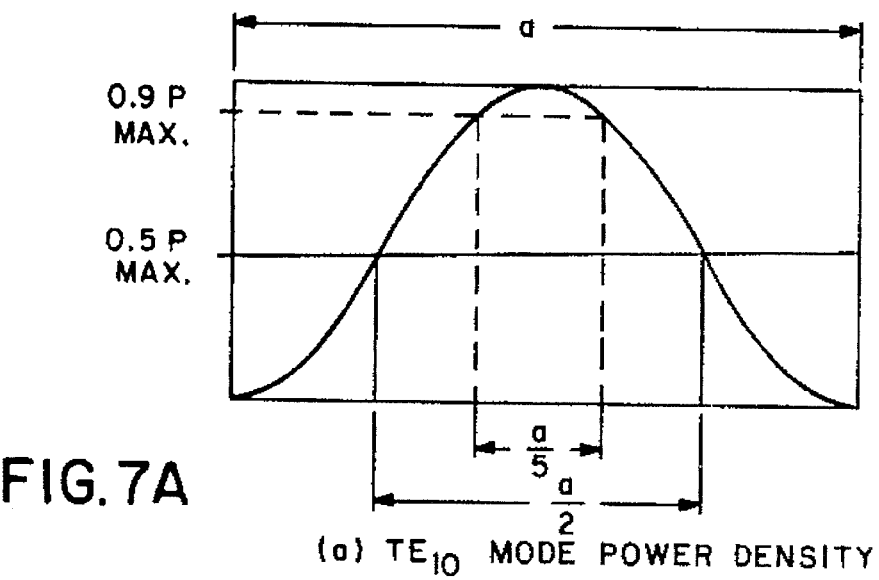
FIGS. 7A, 7B and 7C are graphs of a normalized frequency power density in a single-end driven radio-frequency treatment unit and a radio-frequency treatment unit driven at opposite ends by radio-frequency energy having two different frequencies to provide uniform average power throughout a major portion of the treating chamber of the unit.
Figure 7B:
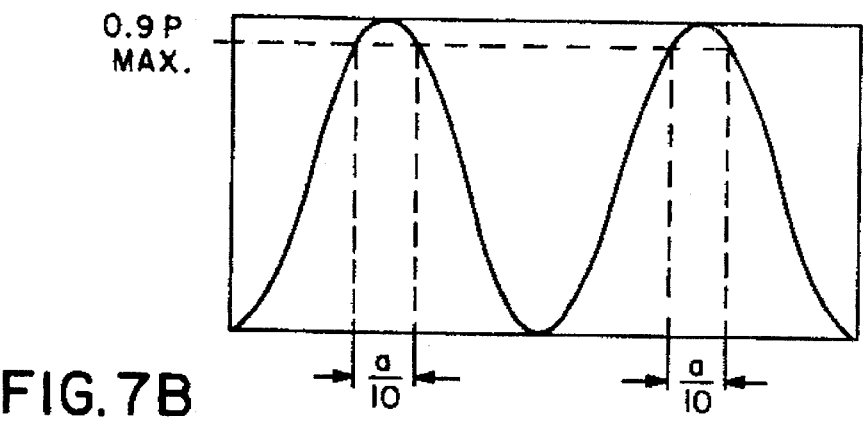
Figure 7C:
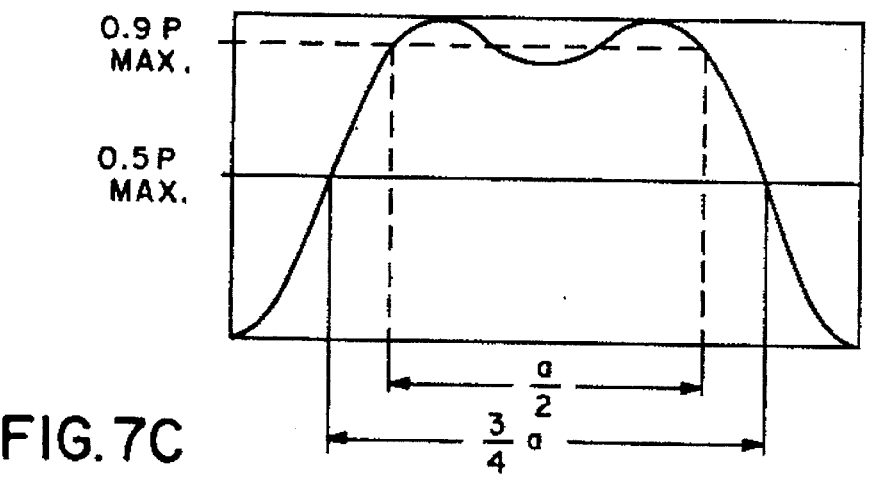

Details of a radio-frequency feed structure for the cavity resonator 32 may best be seen in FIGS. 6A, 6B and 6C. The cavity resonator 32 may in an alternative embodiment be fed from opposite sides by loop-type exciters 310 and 312. The loop exciter 310 is driven at a frequency of 40.68 megahertz while the loop exciter 312 is driven at twice that frequency, 81.36 megahertz. It may be appreciated that this arrangement allows a highly uniform average power to be present within the cavity. As may best be seen in FIG. 7A, a cavity having standing waves induced therein at the lowest mode, has an average power density with a peak at the center of the cavity. If the cavity is driven at a frequency of 81.36 megahertz a pair of power peaks occur, as may be seen in FIG. 7B. The continued effect of the two feeds of the twin feed cavity shown in FIGS. 6A through 6C is shown in FIG. 7C with the power density curve for a relative amplitude for power of 0.864 at the fundamental 40.68 megahertz frequency and a relative amplitude of 0.48 at the first octave or 81.36 megahertz frequency, thereby providing a highly uniform power across three quarters of the distance across the cavity as shown in FIG. 7C. This further provides uniform heating for the medical waste 16 within the cavity.

Figure 9:
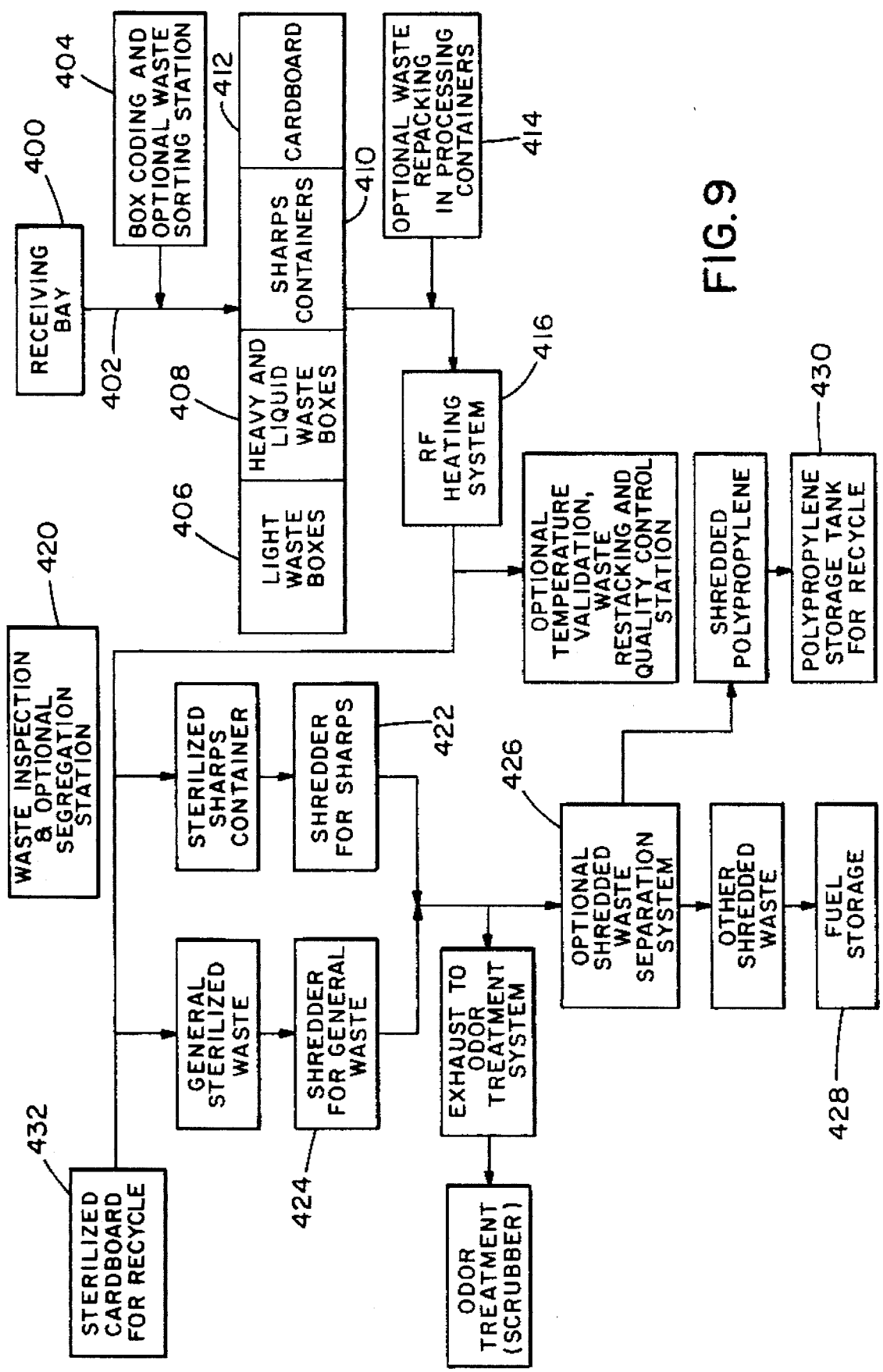
FIG. 9 is a flow diagram showing the steps of waste disinfection carried out by the apparatus of the present invention.

A detailed flow chart of the process steps carried out by the apparatus and method of the present invention is shown in FIG. 9. In step 400, the medical waste is received at a receiving bay and transferred to a belt conveyor in step 402. Optionally, in step 404, the medical waste 16 may be appropriately identified by bar coding or any other identification method and may be sorted according to containerized waste into lightweight boxes in step 406, heavy and liquid waste boxes in step 408, sharps containers in step 410 and possibly cardboard in step 412. Optionally, the medical waste may be repacked in processing containers such as additional boxes of corrugated material in step 414 and then is further transferred by conveyor to a radio-frequency heating system in step 416. The medical waste may be restacked and optional temperature validation procedures may be carried out in step 418.

The medical waste is then segregated in step 420. Disinfected sharps containers are fed to a shredder for sharps containers in step 422. Other material is fed to a shredder for general waste in step 424. The waste may be optionally separated in step 426.

Preliminary to the use of the present invention, medical waste arrives at a processing and recycling facility. Preferably the material is shipped in sealed containers, usually sealed plastic bags. The plastic of the bags does not significantly absorb the radio-frequency energy with which the medical waste is treated. This means of shipping medical materials is known in the art and has the advantage that the medical waste does not infect or contaminate its handlers in transit.

The containers remain in the heating chamber and receive radio-frequency waves for a sufficient time to raise the temperature of the medical materials to approximately 85° C. to 125° C. It will be recognized by those skilled in the art that temperatures as high as 170° C. may be employed without adversely affecting the material to be disinfected. In the disclosed embodiment, the medical waste 16 is moved through the radio-frequency treatment unit 12. The total dose of radio-frequency energy to which the medical waste 16 is exposed during its dwell time in the unit 12 is planned to provide sufficient disinfection.

Preferably, a medical material disinfection facility using the present invention is validated to assure the adequacy of the disinfection process. Validation may be performed when each facility is constructed and at intervals during its operation. Validation may consist of placing heat detecting devices such as thermocouples, resistance temperature detectors, or the like, and/or known amounts of particular microorganisms which are resistant to heat into a load of medical materials. Sufficient radio-frequency energy is applied to raise the temperature of a load to about 85° C. to 125° C. If thermocouples are used, they should all record at least 85° C. indicating that all portions of the load have been heated to at least 85° C. and that there are no cold spots where microorganisms might survive. After the entire disinfection cycle is complete, the microorganism samples are removed from the container and cultured by being given nutrients and other appropriate conditions for growth in order to determine whether any have survived the radio-frequency energy treatment. A typical heat resistant microorganism which may be used in validation of the disinfection process is *Bacillus stearothermophilus*. If more than one in ten thousand of any microorganism survives the exposure to radio-frequency energy, the exposure must be increased and another container tested, and the previously tested container must be retreated with radio-frequency energy. On retest, a temperature of 92° C. may be tried. If that is not adequate, further retests at 94° C., 96° C., and 98° C. may be undertaken until the necessary kill rate is obtained.

The containers are held in the radio-frequency chamber and exposed to radio-frequency waves for a sufficient time to raise the temperature of the medical materials to at least approximately 85° C. It will be recognized by those skilled in the art that temperatures as high as 170° C. will not adversely affect the process. Preferably, the exposure time to radio-frequency waves will vary depending upon the radio-frequency power and the weight of material in order to elevate the temperature of the medical materials to 85° C. to 125° C. and hold that temperature for up to 45 minutes as an extra margin of safety, assuring an even higher kill rate. However, the optimal exposure time to the radio-frequency waves and the field strength of the electromagnetic field of the time-varying field for a particular facility will vary and may be determined as described above.

In a still further embodiment, the load may consist of 18 inch by 18 inch boxes loaded with polyethylene bags filled with hospital waste containing approximately 5 to 10 percent water by weight. In a further embodiment the load may consist of 18"×18" boxes loaded with polyethylene bags filled with shredded hospital waste. Inside each such box an envelope containing test strips loaded with 1×106 spores of *Bacillus subtilis*, var. niger. may be employed. Thermocouple temperature probes also may be placed within and around the boxes.

Another embodiment of the invention consists of starting with medical or veterinary waste that has been presorted into containers of plastic and general medical waste, respectively. High grade plastics are employed in medical products and can be shredded and molded into a variety of other products. This waste is subjected to radio-frequency energy and the containers of disinfected waste are moved to a shredder for the plastics. For example, an electrically powered shredder having a pneumatic ram assist with a negative pressure canopy can shred the medical waste to small particles. Such a shredder may be purchased from Shredding Systems, Inc. of Wilsonville, Oreg., and is identified as a model Dual 1000 E. The negative pressure air canopy removes odors and particles entering the surrounding air and contaminating the atmosphere. The odorous air is then scrubbed and particulates removed by impact filters or electromatic precipitators. The containers or medical waste bags are opened and the disinfected plastic is placed in the shredder and shredded to particles of about one-quarter to one-half inch mean linear dimension. The disinfected shredded plastic is transferred to 55 gallon drums for shipment to plastic recyclers.

Likewise, the containers of disinfected general medical waste may be placed in a general medical waste shredder. After the containers are opened, the disinfected general medical waste is placed in the shredder and shredded to particles have a mean linear dimension of one-quarter to one-half inch. The disinfected waste is placed in further containers containing a mixture of paper, plastic, and metal, which can be used as fuel. Possible users include cement kilns which burn fuel to create temperatures of about 130° C. or more and which might otherwise employ high sulfur coal. Because the general medical waste is low in sulfur, its use as fuel will not generate sulfur compounds which might be released into the atmosphere and contribute to acid rain.

It is believed that part of the superior effectiveness of the radio-frequency heating method disclosed herein is due to the fact that radio-frequency electromagnetic energy penetrates large boxes and volumetrically heats the contents thereof very efficiently. However, this factor alone is not believed to account entirely for the difference observed. It is further believed that the efficacious results of the instant process may be due to the fact that bacteria and viruses have a much higher water content than most of the mixed medical waste. As a result, the relatively high dielectric constant of the bacteria and viruses efficiently couples the electromagnetic or time-varying electromagnetic field energy to the water, causing rapid heating of the microorganisms and subsequent inactivation or destruction thereof. Substances with high dielectric constants selectively absorb radio-frequency energy. Therefore, radio-frequency energy may heat the bacteria and viruses to a lethal temperature before the surrounding waste reaches what is generally considered a lethal temperature.

Individually, the boxes were placed in a two-plate 40 KW radio-frequency heating chamber. The radio-frequency was 18 megahertz. The following parameters were used:

| | | |
|---|---|---|
| Plate KV | = | 13 KVDC |
| Plate Amps | = | 0.5 Amps (No Load) to 0.8 Amps (Loaded) |
| Grid Amps | = | 0.4–0.6 Amps |
| Electrode Height | = | 9.75" (Approximately 1" above box) |
| Time | = | 57 Minutes |
| Temperature | = | 108° C. (maximum internal) |

At the end of the run, the load was allowed to cool. The boxes and individual bags were opened and the spore strips were removed and cultured according to standard techniques. For one run, of thirteen strips, four showed no growth at all. For the nine viable strips, the D-value, or amount of time needed to kill 90% of a test dose, was calculated. For RF, at a maximum temperature of 108° C., the D-value was approximately 9 minutes.

As a control, a dry heat test vessel was used to determine the D-values for *Bacillus subtilis*, var. niger spore strips at 149° C., 160° C., and 179° C. These D-values were graphed and extrapolated to 108° C. At a temperature of 108° C. the D-value for the dry heat process was 20 minutes. Therefore, at a temperature of 108° C. the D-value of 9 minutes for the RF treatment was less than half of the dry heat value. This is evidence that RF heating is markedly more efficient than is the dry heat process, in that it yields a comparable microbial kill rate in significantly shorter time.

At 121° C., the D-value for the RF heating process was 0.31 minutes. A control test of dry heat yielded no kill at this time at any temperature. At 121° C., RF was markedly more effective than the dry heat process.

Figure 15:
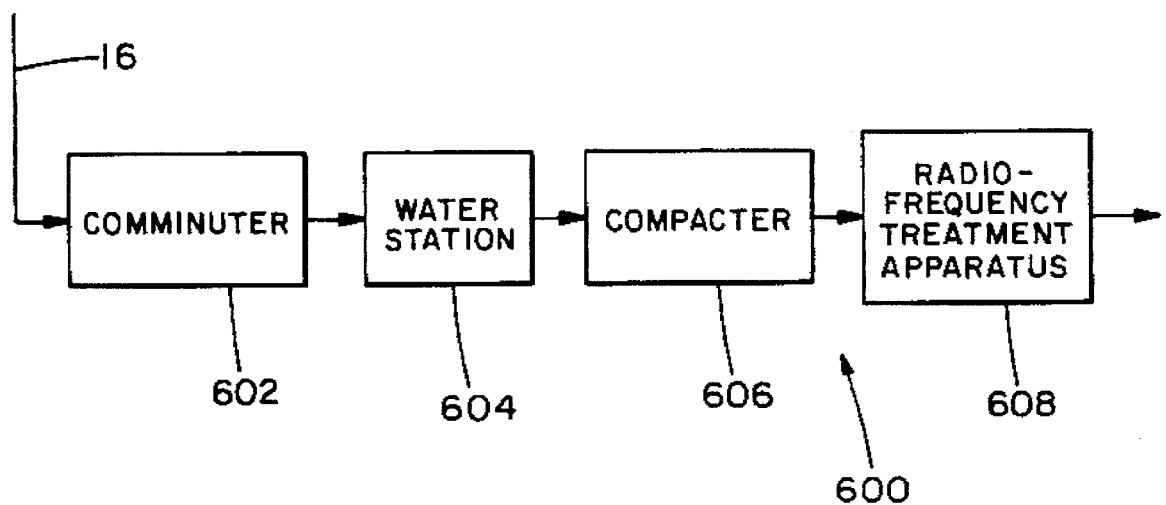
FIG. 15 is a block diagram of another radio-frequency treatment system embodying for disinfecting medical materials.

In a still further alternative embodiment of the present invention, an apparatus 600 for treatment of medical materials, the apparatus 600 as may best be seen in FIG. 15, comprises a comminuter 602 for receiving the waste material 16 from a source of waste. The comminuter receives the containerized waste 16 and transfers it to a water station 604 where water may be added to broken up waste. A compactor 606 is connected to the water station 604 to squeeze or increase the density of the waste to be treated. A radio-frequency treatment apparatus 608, which may either be of the parallel plate type or resonant cavity type, as disclosed hereinabove, receives the compacted waste and heats it to a temperature between 85° C. and 125° C. to disinfect the waste. The treated waste then leaves the radio-frequency treatment apparatus.

Figure 14:
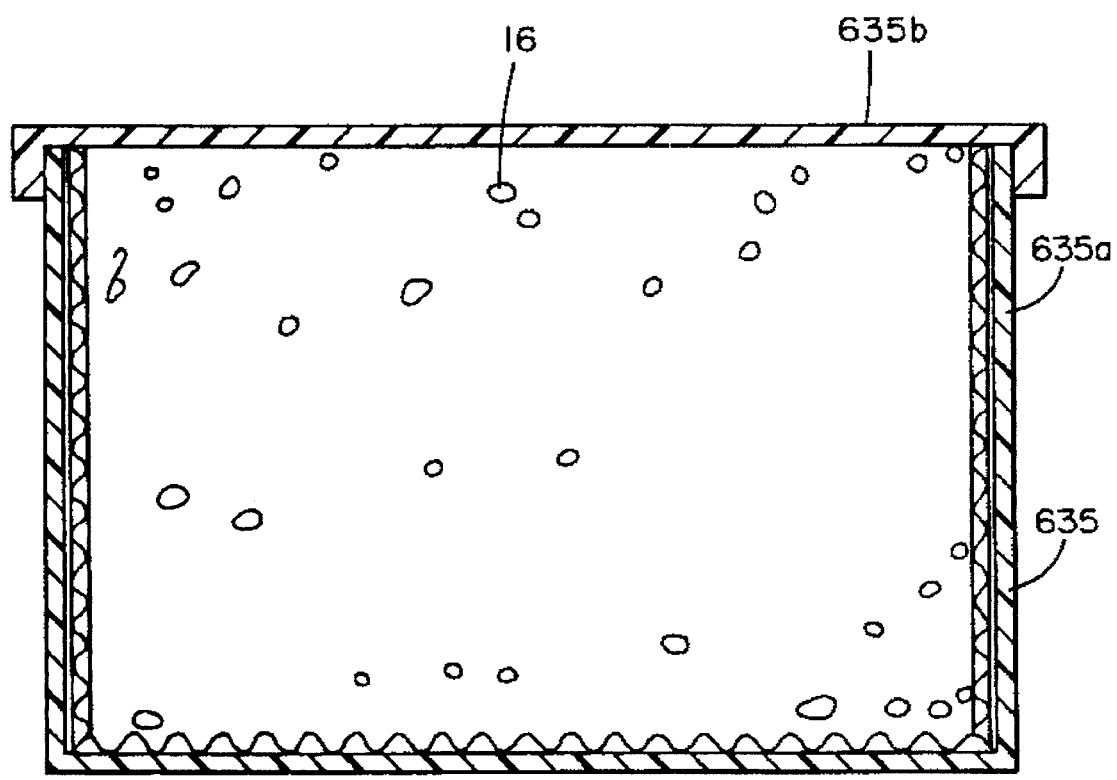
FIG. 14 is sectional view of another container for receiving medical material to be disinfected.
Figure 16:
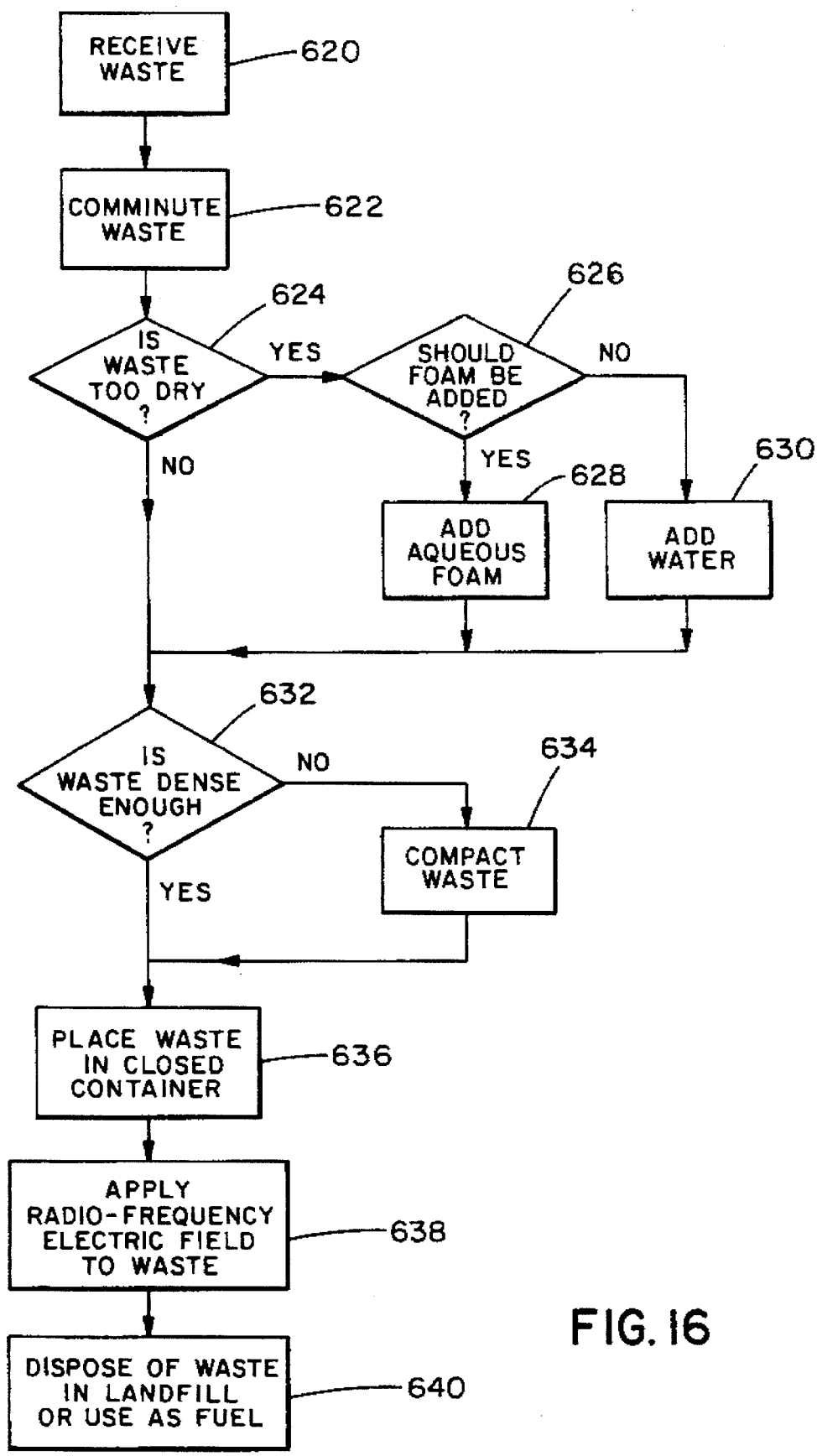
FIG. 16 is a flow diagram of the steps of treating medical materials of the system shown in FIG. 15.

In further detail, as may best be seen in FIG. 16, the medical waste is received in a step 620, the waste is then sent to the comminuter 602 wherein step 622 it is broken into an average particle size of approximately 1 to 2 inches linear dimension. The comminuter 602 may comprise a shredder of the type previously disclosed. The waste is then examined to determine whether water needs to be added in a step 624. If water is to be added, the waste is further examined in a step 626 to determine whether it is desirable to add an aqueous foam, such as a surfactant and water. In the event that foam needs to be added, it is added in a step 628 in water station 604. If foam need not be added, water is added in a step 630. The material having the additional water either in the form of foam or pure water, is then examined to determine whether the waste is dense enough. Likewise, waste which is not too dry which is adequately wetted is also examined. If it is considered not to be dense enough, the waste is compacted in a step 634 in the compactor 606 to achieve a higher desired density. The proper density waste 16 then, as shown in FIG. 14, is placed in a closed container 635 having a body 635a and a top 635b fitted to the body 635a which may be comprised of an epoxy filled with fiberglass which closed container may either be able to maintain pressure slightly above atmospheric or up to 15 pounds per square inch above atmospheric pressure. The container is then placed in the radio-frequency treatment apparatus which may either be a parallel plate type or resonant cavity in which should be excited between 10 megahertz and 100 megahertz. If the waste container 635 is not rated at a pressure of 15 pounds per square inch above atmospheric pressure, the radio-frequency treatment apparatus itself may be pressurized so that the waste may be adequately heated therein. When the electric field is applied to the waste 16 by the radio-frequency treatment apparatus 608 in the step 638 waste 16 having water thereon or therein is rapidly heated liberating vapor which travels to portions of the waste which do not have water thereon. The water vapor then condenses on the dry portions of the waste 16, having been confined in proximity with the drier waste by the closed container. The water vapor transfers its heat of vaporization to the previously dry waste and increases its radio-frequency energy absorption. The waste is then additionally heated by transfer of energy from the radio-frequency electric field which heats the condensed water within or on the previously dry waste. In the event that the container 635 can withstand a pressure over atmospheric, the waste may be heated to above 100° C. preferably to 100–125° C. If the radio-frequency treatment apparatus and container are only able to maintain the waste 16 at atmospheric pressure, the waste will be heat to 90° C.–100° C.

One of the advantages of the instant process is that when the waste 16 is comminuted, dielectric materials in the waste 16 are brought into close contact with the metal-containing portions of the waste thereby reducing the likelihood of arcing. In addition, arcing is reduced by the addition of the foam or water which would tend to quench the arc and in addition prevent combustible materials in the waste from burning should arcing occur when the radio-frequency electric field is applied. The closed container 635 also helps to prevent unwanted combustion of the waste 16 while it is being heated by the radio-frequency electric field since the amount of oxygen within the container is limited and would be rapidly used when combustion starts. The container itself, being made of a combination of epoxy and fiberglass, can withstand temperatures of up to 400° F. before being damaged by the heated. Thus, the container is substantially combustion resistant.

In order to render the process more efficient, the aqueous foam may be added in the step 628 which provides an absorbing dielectric in contact with metal portions of the comminuted waste to prevent combustion due to arcing but which reflects relatively little radio-frequency energy directed into the waste. This is due to the fact that such a foam aqueous dieelectric typically has a dieelectric constant of 2 which would result in a reflection of only about 10% of the power directed at the waste 16. While liquid water, having a dieelectric constant of 80 would reflect almost 90% of the radio-frequency power fed to comminuted waste.

The process is also further rendered efficient by the use of the compaction step 634 which allows more waste to be processed within the radio-frequency treatment apparatus in a selected period of time. It may be appreciated, however, that the compaction could not occur to any indefinite degree as the amount of material to be heated may be so increased that the time in which heating takes place might be significantly slowed. In any event, compaction of the waste from 5 or 10 pounds per cubic foot, which is the density of the waste as it is received from hospitals and the like, to a density of 25 to 30 lbs. per cubic foot would not significantly effect the heating time.

The foregoing descriptions of the preferred embodiments of the present invention have been presented for purposes of illustration and description. They are not intended to be exhaustive or to limit the invention to the precise forms disclosed, and obviously many other modifications and variations are possible in light of the aforementioned teachings. The embodiments were chosen and described to best explain the principles of the invention and its practical applications, thereby enabling others skilled in the art to utilize best the invention in its various embodiments and with various modifications as are suited to the particular use contemplated.

What is claimed is:

1. A method of disinfecting and processing dielectrically heterogeneous bulk medical waste to inactivate pathogens, comprising the steps of:

comminuting the dielectrically heterogeneous medical waste into comminuted dielectrically heterogeneous medical waste particles having a predetermined size;

placing the comminuted dielectrically heterogeneous medical waste particles in a bulk dielectric processing container;

conveying the bulk dielectric processing container with the comminuted dielectrically heterogeneous medical waste particles therein through an Opening and into a treatment region of a treatment chamber; and applying within the treatment region a transverse mode radio-frequency electric field from a pair of parallel plates, the transverse mode radio frequency electric field having a frequency in the range of about 3 megahertz to about 80 megahertz, the transverse mode radio frequency electric field heating the comminuted dielectrically heterogeneous medical waste particles to a temperature of 85° C. to 125° C., the transverse mode radio-frequency electric field substantially penetrating the comminuted dielectrically heterogeneous bulk medical waste particles and exhibiting a square of the electric field strength that varies by no more than a factor of two in the treatment region to produce disinfected comminuted dielectrically heterogeneous medical waste particles without substantially producing ionized gas.

2. A method of disinfecting and processing dielectrically heterogeneous bulk medical waste to inactivate pathogens according to claim 1, wherein the step of comminuting the dielectrically heterogeneous bulk medical waste comprises reducing the dielectrically heterogeneous bulk medical waste to comminuted dielectrically heterogeneous bulk medical waste particles in a size range of 0.25 to 0.50 inch.

3. A method of disinfecting and processing dielectrically heterogeneous medical waste to inactivate pathogens according to claim 1, wherein the step of applying the transverse mode radio-frequency electric field lasts for a duration of at least approximately 5 minutes.

4. A method of disinfecting and processing dielectrically heterogeneous medical waste to inactivate pathogens according to claim 1, wherein the step of applying the transverse mode radio-frequency electric field lasts for a duration of between 3 and 30 minutes.

5. A method of disinfecting and processing dielectrically heterogeneous medical waste to inactivate pathogens according to claim 1, further comprising, the step of sorting the dielectrically heterogeneous medical waste into plastics waste and general medical waste and placing the plastics waste and general medical waste into separate processing containers for plastics waste and general medical waste, respectively.

6. A method of disinfecting and processing dielectrically heterogeneous medical waste to inactivate pathogens according to claim 5, further comprising recycling the sorted medical waste by reusing the disinfected plastic waste and using the disinfected general medical waste as fuel.

7. A method of disinfecting and processing dielectrically heterogeneous medical waste to inactivate pathogens comprising the steps of:

comminuting the dielectrically heterogeneous bulk medical waste into comminuted dielectrically heterogeneous medical waste particles having a predetermined size;

placing one of the comminuted dielectrically heterogeneous medical waste particle types in a bulk dielectric processing container;

adding water to the dielectrically heterogeneous comminuted medical waste particles;

conveying the bulk dielectric processing container with the comminuted dielectrically heterogeneous medical waste particles therein through an opening and into a treatment chamber; and applying within the treatment chamber for about five minutes a transverse mode radio-frequency electric field from a pair of parallel plates, the transverse mode radio-frequency electric field having a frequency in the range of about 3 megahertz to about 80 megahertz, the transverse mode radio-frequency electric field heating the comminuted dielectrically heterogeneous medical waste particles to a temperature of about 85° C. to about 125° C., the transverse mode radio-frequency electric field substantially penetrating the comminuted dielectrically heterogeneous bulk medical waste particles and disinfecting the comminuted dielectrically heterogeneous medical waste particles without substantially producing ionized gas.

8. A method of disinfecting and processing dielectrically heterogeneous medical waste to inactivate pathogens according to claim 7, wherein the step of adding water further comprises adding a foam comprising water and a surfactant to the dielectrically heterogeneous comminuted medical waste particles.

9. A method of disinfecting and processing dielectrically heterogeneous medical waste to inactivate pathogens according to claim 7, further comprising the step of compacting the comminuted dielectrically heterogeneous medical waste particles.

10. A method of disinfecting and processing dielectrically heterogeneous medical waste to inactivate pathogens according to claim 7, further comprising the step of separating the dielectrically heterogeneous medical waste into material comprising plastic and refuse-derived fuel.

\* \* \* \* \*